(12) United States Patent
Dueva-Koganov et al.

(10) Patent No.: US 11,154,493 B2
(45) Date of Patent: Oct. 26, 2021

(54) MITIGATING ADVERSE EFFECTS OF SUNLIGHT WITH INGREDIENTS OBTAINED FROM LIVING PLANTS

(71) Applicant: ISP INVESTMENTS LLC, Wilmington, DE (US)

(72) Inventors: Olga Dueva-Koganov, White Plains, NY (US); Artyom Duev, White Plains, NY (US); Li Zhang, Princeton, NJ (US); Karine Cucumel, Opio (FR); Gilles Oberto, Valbonne (FR)

(73) Assignee: ISP INVESTMENTS LLC, Wilmington, DE (US)

( * ) Notice: Subject to any disclaimer, the term of this patent is extended or adjusted under 35 U.S.C. 154(b) by 0 days.

(21) Appl. No.: 16/078,925

(22) PCT Filed: Feb. 27, 2017

(86) PCT No.: PCT/US2017/019672
§ 371 (c)(1),
(2) Date: Aug. 22, 2018

(87) PCT Pub. No.: WO2017/147578
PCT Pub. Date: Aug. 31, 2017

(65) Prior Publication Data
US 2019/0282491 A1 Sep. 19, 2019

Related U.S. Application Data

(60) Provisional application No. 62/299,614, filed on Feb. 25, 2016.

(51) Int. Cl.
*A61K 8/9789* (2017.01)
*A61Q 19/08* (2006.01)

(52) U.S. Cl.
CPC ............ *A61K 8/9789* (2017.08); *A61Q 19/08* (2013.01); *A61K 2800/805* (2013.01); *A61K 2800/81* (2013.01)

(58) Field of Classification Search
CPC ............................ A61Q 19/08; A61K 8/9789
See application file for complete search history.

(56) References Cited

U.S. PATENT DOCUMENTS

| 5,902,587 | A | 5/1999 | Carle et al. |
| 7,442,391 | B2* | 10/2008 | Koganov ............... A61K 8/97 424/400 |
| 2012/0237460 | A1* | 9/2012 | Swanson ............... A61K 8/97 424/59 |
| 2013/0323339 | A1* | 12/2013 | Koganov ............... A61K 8/97 424/769 |
| 2015/0157557 | A1 | 6/2015 | Osborne et al. |
| 2015/0258012 | A1 | 9/2015 | Koganov |

FOREIGN PATENT DOCUMENTS

| CN | 1076555 A | 7/2010 |
| KR | 100828193 B1 * | 5/2008 |
| WO | WO-2014076055 A1 * | 5/2014 |

OTHER PUBLICATIONS

International Search Report of PCT Application No. PCT/US2017/019672 published on Aug. 31, 2017.

* cited by examiner

*Primary Examiner* — Robert A Wax
*Assistant Examiner* — William Craigo
(74) *Attorney, Agent, or Firm* — William J. Davis; Nathalie Tietcheu

(57) ABSTRACT

Disclosed herein are methods of improving skin appearance associated with skin aging. The method comprises the step of applying an anti-aging bioactive composition to a skin surface having at least one sign of aging. The anti-aging bioactive composition is applied for a period of time sufficient to improve the appearance of the at least one sign of aging. In one embodiment, the anti-aging bioactive composition comprises an effective amount of a *Nelumbo nucifera* (Sacred Lotus) serum fraction. In another embodiment, the anti-aging bioactive composition comprises an effective amount of a *Chamomilla recutita* (German Chamomile) Flower serum fraction. In other embodiments, the anti-aging bioactive composition can further include a dermatologically acceptable carrier.

4 Claims, 7 Drawing Sheets

MITIGATING ADVERSE EFFECTS OF SUNLIGHT WITH INGREDIENTS OBTAINED FROM LIVING PLANTS

CROSS-REFERENCE TO RELATED APPLICATIONS

This application claims priority benefit of U.S. Provisional Patent Application Ser. No. 62/299,614, filed Feb. 25, 2016, the disclosure of which is hereby incorporated by reference herein in its entirety.

FIELD OF THE DISCLOSURE

The present disclosure relates to, inter alia, the field of cosmetics and more specifically to the field of mitigating adverse effects of sunlight with ingredients obtained from living plants.

BACKGROUND OF THE INVENTION

Damaging effects of sunlight on human skin are well known. Overly high exposure leads to acute adverse reaction involving irritation and inflammation, such as UV induced sunburn. However, more than 90% of full solar radiation spectrum is in the VIS-IR range, and its potential contribution to skin damage is being increasingly recognized. Sun exposures energetically insufficient to cause acute skin reaction can still trigger inflammation-related processes; and accumulated inflammatory damage significantly contributes to degradation of skin resilience and development of undesirable appearance, in a process known as photoaging.

The present invention is directed to overcoming these and other deficiencies in the art.

SUMMARY OF THE INVENTION

Disclosed herein are, inter alia, methods of cosmetic care to mitigate adverse effects of sunlight with ingredients obtained from living plants, including the topical application, on at least a portion of the skin of the body or the face, of biologically active ingredients of the present invention that were obtained from fresh (living) whole plants of *Nelumbo nucifera* Gaertn. (Sacred Lotus) and from fresh (living) flowers collected from *Chamomilla recutita* (German Chamomile).

In one aspect, the present disclosure provides a method of improving skin appearance associated with skin aging using a *Nelumbo nucifera* (Sacred Lotus) serum fraction. This method comprises the step of applying an anti-aging bioactive composition to a skin surface having at least one sign of aging, where the anti-aging bioactive composition comprises an effective amount of *Nelumbo nucifera* (Sacred Lotus) serum fraction. The anti-aging bioactive composition is applied for a period of time sufficient to improve the appearance of the at least one sign of aging. In certain embodiments of this method, the anti-aging bioactive composition further comprises a dermatologically acceptable carrier.

In another aspect, the present disclosure provides a method of improving skin appearance associated with skin aging using a *Chamomilla recutita* (German Chamomile) Flower serum fraction. This method comprises the step of applying an anti-aging bioactive composition to a skin surface having at least one sign of aging, where the anti-aging bioactive composition comprises an effective amount of *Chamomilla recutita* (German Chamomile) Flower serum fraction. The anti-aging bioactive composition is applied for a period of time sufficient to improve the appearance of the at least one sign of aging. In certain embodiments of this method, the anti-aging bioactive composition further comprises a dermatologically acceptable carrier.

In accordance with the present disclosure, it was unexpectedly found that the serum fractions described herein each has a combination of various advantageous properties associated with mitigating the adverse effects of skin aging. Such advantageous properties include, without limitation, the following: (i) beneficial spectral absorbance characteristics in UVA-UVB area; (ii) high UVA:UVB absorbance ratios in conjunction with broad UVA and UVB spectral absorption photostability demonstrated after full spectrum simulated sun exposures (noting that the calculation of the UVA:UVB absorbance ratio could yield values from zero (equal to no UVA absorbance) up to 1.0 (UVA absorbance equal to UVB)); (iii) increased attenuation in UVA1 area and simultaneous increase in UVA/UVB ratio as the radiation dose increased, which is an unusual, desirable and not anticipated property; (iv) potent biological activities (properties) demonstrated in various in vitro cell culture based bioassays associated with full spectrum simulated sun exposure and relevant enzymatic models; (v) maintenance of more than 95% of initial (pre-irradiation) DPPH quenching capacities after 4 MED exposure delivered by full spectrum simulated sunlight, which confirms their photostability from the performance point of view; and (vi) combinations thereof. The serum fractions of the present disclosure where also found to provide multifunctional activities that work together to mitigate various adverse effects of full spectrum sunlight exposure on skin cells.

Another advantage of the serum fractions and methods of the present disclosure over existing skin aging products and methods is that the serum fractions are derived from living plants using a fractionation process not found in nature. Further, as described herein, the serum fractions obtained from living plants are water-soluble/miscible and do not require the use of an inorganic particulate material, such zinc oxide. Additionally, the serum fractions of the present disclosure are advantageous in that they are capable of mitigating various adverse effects of sun exposure, which such inorganic particulate materials like zinc oxide are arguably not capable of doing.

Yet another advantage of the serum fractions and methods of the present disclosure over existing skin aging products and methods includes the excellent safety and toxicity profile of the serum fractions. As shown herein, based on the advantageous safety/toxicity profile, it is feasible that the serum fractions of the present disclosure can be used, if necessary or desirable, at concentrations much higher than skin aging products in the art. While some skin aging products known in the art may have an upper limit of active ingredient of about 15% by total weight, the serum fractions of the present disclosure can be used "as is" (i.e., at 100% as supplied) for some applications.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, if provided, like reference numerals contained in the drawings are meant to identify similar or identical elements.

DETAILED DESCRIPTION

Figure 1:
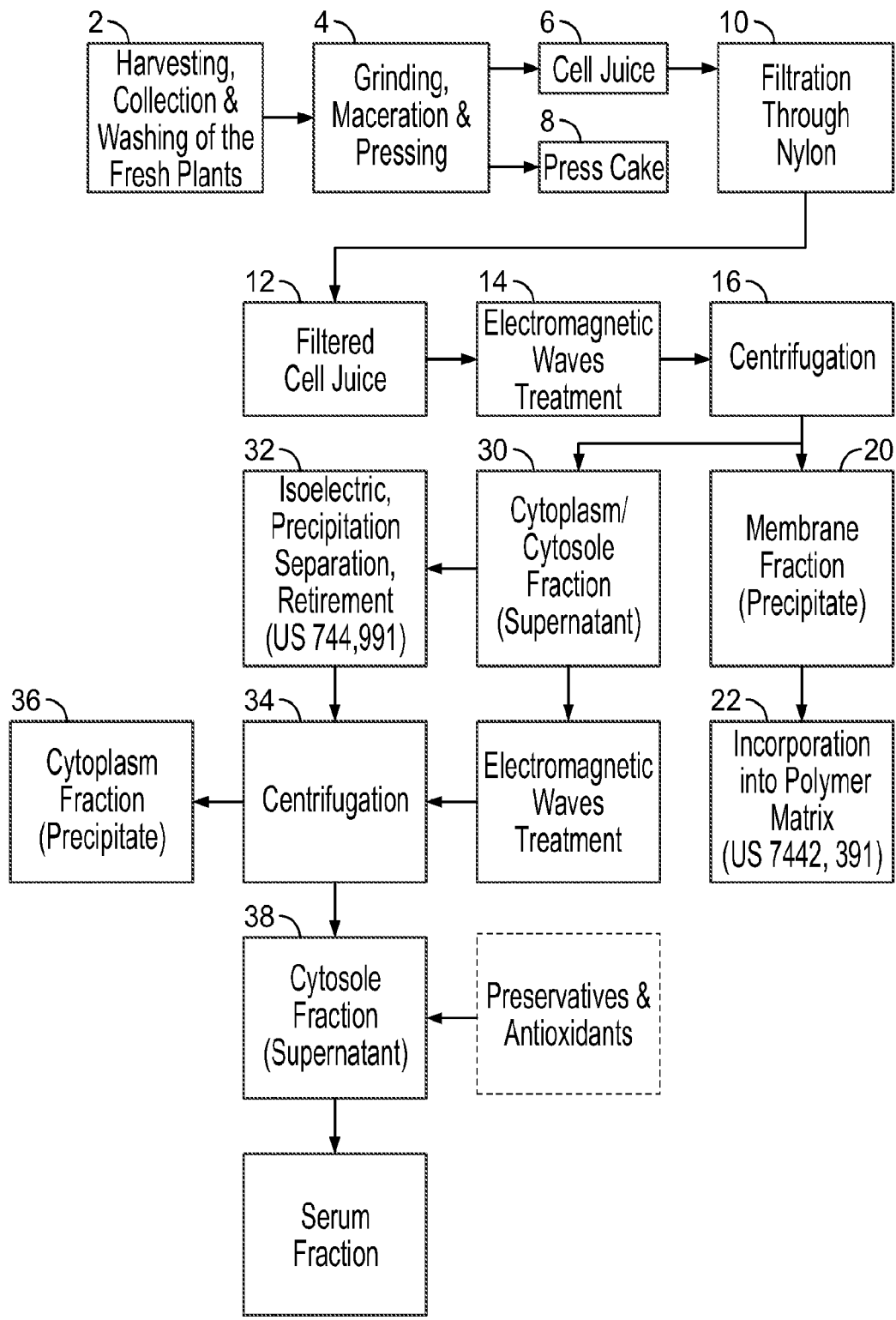
FIG. 1 is a schematic drawing demonstrating one embodiment of a process for preparing the bioactive anti-aging ingredients of the present invention.

The present disclosure provides, inter alia, methods for mitigation of adverse effects of sunlight on skin. The present disclosure also relates to a method of cosmetic care including the topical application, on at least a portion of the skin of the body or the face, of biologically active ingredients of the present invention obtained from fresh (living) whole plants of *Nelumbo nucifera* Gaertn. (Sacred Lotus) and from fresh (living) flowers collected from *Chamomilla recutita* (German Chamomile). The present disclosure also relates methods for preparing these bioactive botanical cosmetic compositions and the uses of these compositions in various formulations and as topical skin applications.

All numeric ranges described herein are inclusive of narrower ranges; delineated upper and lower range limits are interchangeable to create further ranges not explicitly delineated.

The compositions described and used in the present disclosure can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition means to apply or spread the compositions of the present invention onto a human skin surface such as the epidermis.

The term "dermatologically acceptable" as used herein means that the compositions or components described are suitable for use in contact with human skin tissue without undue toxicity, incompatibility, instability, allergic response, and the like.

The term "effective amount" as used herein means an amount of a compound or composition sufficient to significantly induce a positive appearance and/or feel benefit, but low enough to avoid serious side effects (i.e., to provide a reasonable benefit to risk ratio, within the scope of sound judgment of the skilled artisan).

In one aspect, the present disclosure provides a method of improving skin appearance associated with skin aging. The method comprises the step of applying an anti-aging bioactive composition to a skin surface having at least one sign of aging. The anti-aging bioactive composition is applied for a period of time sufficient to improve the appearance of the at least one sign of aging.

In a particular aspect, the present disclosure provides a method of improving skin appearance associated with skin aging using a *Nelumbo nucifera* (Sacred Lotus) serum fraction. This method comprises the step of applying an anti-aging bioactive composition to a skin surface having at least one sign of aging, where the anti-aging bioactive composition comprises an effective amount of *Nelumbo nucifera* (Sacred Lotus) serum fraction. The anti-aging bioactive composition is applied for a period of time sufficient to improve the appearance of the at least one sign of aging.

In one embodiment, the effective amount of said *Nelumbo nucifera* (Sacred Lotus) serum fraction is in a range of from 0.001% to 100% by weight of the total composition.

In one embodiment, the anti-aging bioactive composition comprises an effective amount of *Nelumbo nucifera* (Sacred Lotus) serum fraction and a dermatologically acceptable carrier. In more particular embodiments, the anti-aging bioactive composition comprises, by weight of the total composition, from 0.001% to 99% of said *Nelumbo nucifera* (Sacred Lotus) serum fraction.

In another aspect, the present disclosure provides a method of improving skin appearance associated with skin aging using a *Chamomilla recutita* (German Chamomile) Flower serum fraction. This method comprises the step of applying an anti-aging bioactive composition to a skin surface having at least one sign of aging, where the anti-aging bioactive composition comprises an effective amount of *Chamomilla recutita* (German Chamomile) Flower serum fraction. The anti-aging bioactive composition is applied for a period of time sufficient to improve the appearance of the at least one sign of aging.

In one embodiment, the effective amount of said *Chamomilla recutita* (German Chamomile) Flower serum fraction is in a range of from 0.001% to 100% by weight of the total composition.

In one embodiment, the anti-aging bioactive composition comprises an effective amount of *Chamomilla recutita* (German Chamomile) Flower serum fraction and a dermatologically acceptable carrier. In more particular embodiments, the anti-aging bioactive composition comprises, by weight of the total composition, from 0.001% to 99% of said *Chamomilla recutita* (German Chamomile) Flower serum fraction.

In accordance with the present disclosure, the anti-aging bioactive composition mitigates adverse effects of exposure of skin to sunlight.

In accordance with the present disclosure, the anti-aging bioactive composition has multifunctional activities that work synergistically to mitigate adverse effects of full spectrum sunlight exposure on skin cells.

In accordance with the present disclosure, the anti-aging bioactive composition is effective in improving skin appearance attributes associated with skin aging by improving skin hydration, skin barrier function, skin laxity, skin appearance of wrinkles, drainage and body contouring, skin pigmentation, and/or skin tone.

In accordance with the present disclosure, the anti-aging bioactive composition has a synergistic combination of properties selected from the group consisting of the following: (i) beneficial spectral absorbance characteristics in UVA-UVB area; (ii) high UVA:UVB absorbance ratios in conjunction with broad UVA and UVB spectral absorption photostability demonstrated after full spectrum simulated sun exposures; (iii) increased attenuation in UVA1 area and simultaneous increase in UVA/UVB ratio as radiation dose is increased; (iv) potent biological activities (properties) demonstrated in various in vitro cell culture based bioassays associated with full spectrum simulated sun exposure and relevant enzymatic models; (v) maintenance of more than 95% of initial (pre-irradiation) DPPH quenching capacities after 4 MED exposure delivered by full spectrum simulated sunlight; (vi) multifunctional activities that work together to mitigate various adverse effects of full spectrum sunlight exposure on skin cells; and (vii) combinations thereof.

In accordance with various embodiments of the methods of the present disclosure, the skin surface is selected from the group consisting of a body skin surface and a facial skin surface.

In certain embodiments of the methods of the present disclosure, the anti-aging bioactive composition further comprises an additional ingredient selected from the group consisting of a sunscreen active, an anti-inflammatory agent, and a skin tone agent.

In other embodiments of the methods of the present disclosure, the anti-aging bioactive composition is applied to a plurality of signs of skin aging for a period of time sufficient to improve the appearance of the plurality of signs of skin aging.

In accordance with the methods of the present disclosure, the *Nelumbo nucifera* (Sacred Lotus) serum fraction or the *Chamomilla recutita* (German Chamomile) Flower serum fraction is isolated using a fractionation process not found in nature. In one embodiment, the fractionation process comprises subjecting plant cell juice derived from fresh plant biomass of the *Nelumbo nucifera* (Sacred Lotus) plant or the *Chamomilla recutita* (German Chamomile) flowers to an electromagnetic field at a frequency of greater than 2.45 GHz for a time effective to destabilize the plant cell juice yielding a coagulated cell juice mixture comprising a coagulated membrane fraction, and separating said coagulated membrane fraction from said coagulated cell juice mixture in order to yield a bioactive fraction comprising a cytoplasm/cytosole fraction that is substantially-free from said membrane fraction, followed by additional treatments enabling to separate cytoplasm fraction from cytosole fraction that is stabilized to yield the serum fraction (FIG. 1).

As described above, once the plant cell juice is separated into membrane fraction and a cell juice supernatant, i.e. cytoplasm/cytosole fraction 30 which is subjected to additional treatments enabling to separate cytoplasm fraction from cytosole fraction.

The quantitative criteria to evaluate the complete separation of cytoplasm fraction is the absence of detectable levels of high molecular weight proteins and/or the absence of ribulose 1,5-biphosphate carboxilase oxygenase in cytosole fraction.

The cytosole fraction contains low molecular weight water soluble components dissolved in the intracellular water. The cytosole fraction is clear liquid which has a yellow color and slight characteristic odor. In several hours, the unstable cytosole fraction is irreversibly transformed into dark brown color suspension containing heavy precipitate and strong non-characteristic odor. As a result, cytosole fraction cannot be used as a cosmetic ingredient. The described procedure that follows allows for the refinement of cytosole fraction to yield stable and active serum fraction. This is accomplished by removing from cytosole fraction the major components responsible for the irreversible transformations that lead to generation of unwanted precipitate and deterioration of color and odor. This procedure includes: pH adjustment, heat treatment, cooling, vacuum filtration, and stabilization as described in U.S. Pat. Nos. 7,442,391, 8,101, 212, 8,277,852 and 8,318,220, which are all incorporated herein by reference.

After the cytosole fraction is produced, it is then subjected to the stabilizing step to yield the Serum Fraction (FIG. 1). Suitable agents for use in the stabilizing step of present invention include, but are not limited to potassium sorbate, sodium benzoate, sodium methyl paraben, tetrasodium EDTA, pentylene glycol, sodium metabisulfite.

Bioactive ingredients in accordance with the present disclosure can be obtained from fresh (living) whole plants of *Nelumbo nucifera* Gaertn. (Sacred Lotus) and from fresh (living) flowers collected from *Chamomilla recutita* (German Chamomile) according to the process described in U.S. Pat. Nos. 7,442,391; 7,473,435; 7,537,791; 8,043,635; 8,101,212; 8,277,852; 8,318,220; U.S. Pat. Application Publication Nos. US-2015/0258012A1 and US-2016/0000851A1; and PCT/EP2013/073565, the disclosures of which are all incorporated herein by reference, and evaluated for their abilities to mitigate various adverse effects of sunlight.

The serum fractions used in the methods of the present invention are not naturally occurring, but instead are produced using a manmade manufacturing process. In one embodiment, this manufacturing process employs grinding and pressing fresh living plants (also referred to as fresh plant biomass) in order to obtain a plant cell juice (intracellular colloidal dispersion), and treat it with an electromagnetic waves at a frequency effective to initiate separation of membrane fraction from cell juice in order to yield a cell cytoplasm/cytosole fraction substantially free from membrane fraction. The cytoplasm/cytosole fraction is further processed under conditions effective to separate the cytoplasm/cytosole fraction into its component parts, e.g. cytoplasm fraction and a cytosole fraction. The process for the preparation of botanical fractions from fresh plant biomass used in the present invention comprises grinding (or maceration) and pressing fresh plant biomass in order to obtain an intracellular plant material, referred to herein as plant cell juice, containing membrane fractions, and treating said cell juice with an electromagnetic waves at a frequency effective to trigger separation of said membrane fraction from said cell juice fraction in order to yield a cell cytoplasm/cytosole fraction substantially-free from membrane fractions. The aforementioned treatment is advantageously performed such that the temperature of said cell juice during said treatment does not exceed 40° C. The membrane fractions can then be utilized in order to provide a stable botanical cosmetic composition exhibiting antiproteolytic, cell growth inhibition activity, and/or both antiproteolytic and cell growth inhibition activities, where the antiproteolytic activity is due to inhibition of at least one proteinase and the cell growth inhibition activity is due to inhibition of cell growth of at least one type of cell. The cytoplasm/cytosole fraction can be utilized in order to provide a botanical composition suitable for use as a component in a pharmaceutical, cosmetic, nutritional, therapeutic and/or personal care formulation and the like. The cytoplasm/cytosole fraction is further processed under conditions effective to separate the cytoplasm/cytosole fraction into its component parts, namely the cytoplasm fraction and a cytosole fraction. The cytoplasm fraction includes predominantly proteins.

By way of example, the overall process for preparing the bioactive botanical cosmetic compositions of the present invention is described below in reference to FIG. 1. As depicted in FIG. 1, fresh living plants are harvested, collected, and washed to yield fresh plant biomass 2. This fresh plant biomass is subjected to grinding, maceration, and pressing 4 to yield intracellular plant material (cell juice) 6 and fiber-enriched material (press-cake) 8. Cell juice 6 is then filtered through nylon mesh 10 to yield filtered plant cell juice 12. Filtered cell juice 12 is exposed to electromagnetic waves treatment 14 at a frequency to trigger its destabilization. The destabilized cell juice is and then subjected to centrifugation 18 in order to yield precipitated membrane fraction 20 and a supernatant which is cytoplasm/cytosole fraction 30. Membrane fraction 20 is a bioactive botanical cosmetic composition which can be added into cosmetic products as described for example, in U.S. Pat. Nos. 7,442,391, 8,101,212, 8,277,852 and 8,318,220. Plant cytoplasm/cytosole fraction 30 is used for further processes, as described below.

Cytoplasm/cytosole fraction 30 is subjected to additional treatments: i, ii, iii or iv. as summarized below. As a non-limiting example, treatment (i) can include isoelectric precipitation 32 and following centrifugation 34 enabling to separate precipitated cytoplasm fraction 36 from supernatant containing cytosole fraction 38, as described for example, in U.S. Pat. Nos. 7,442,391, 8,101,212, and 8,277,852. Alternatively, cytosole/cytoplasm fraction can be further separated as result of (ii) additional electromagnetic treatment (at frequency >7 GHz) with following centrifugation or filtration, or (iii) membrane filtration, or (iv) ultrafiltration, or combination of thereof (i, ii, iii, iv). Cytoplasm/cytosole fraction components can be utilized "as is" or can be further separated and utilized. They can also be stabilized with preservatives and antioxidants as described for example, in U.S. Pat. Nos. 7,442,391; 7,473,435; 7,537,791; 8,043,635; 8,101,212; 8,277,852 and 8,318,220.

As described above, once the plant cell juice is separated into membrane fraction and a cell juice supernatant, i.e. cytoplasm/cytosole fraction 30 which is subjected to additional treatments: i, ii, iii or iv (FIG. 1) enabling to separate cytoplasm fraction from cytosole fraction.

The quantitative criteria to evaluate the complete separation of cytoplasm fraction is the absence of detectable levels of high molecular weight proteins and/or the absence of ribulose 1,5-biphosphate carboxylase oxygenase in cytosole fraction.

The cytosole fraction contains low molecular weight water soluble components dissolved in the intracellular water. The cytosole fraction is clear liquid which has a yellow color and slight characteristic odor. In several hours, the unstable cytosole fraction is irreversibly transformed into dark brown color suspension containing heavy precipitate and strong non-characteristic odor. As a result, cytosole fraction cannot be used as a cosmetic ingredient. The described procedure that follows allows for the refinement of cytosole fraction to yield stable and active serum fraction which is stable cosmetic ingredient. This is accomplished by removing from cytosole fraction the major components responsible for the irreversible transformations that lead to generation of unwanted precipitate and deterioration of color and odor. This procedure includes: pH adjustment, heat treatment, cooling, vacuum filtration, and stabilization as described in U.S. Pat. Nos. 7,442,391, 8,101,212, 8,277,852 and 8,318,220, which are all incorporated herein by reference.

After the cytosole fraction is produced, it is then subjected to the stabilizing step to yield the Serum Fraction (Serum-Derived Cosmetic Composition). Suitable agents for use in the stabilizing step of present invention include, but are not limited to potassium sorbate, sodium benzoate, sodium methyl paraben, tetrasodium EDTA, pentylene glycol, sodium metabisulfite.

Suitable preservatives for use in the present invention include, but are not limited to potassium sorbate, sodium benzoate.

An example of a suitable antioxidant for use in the present invention is sodium metabisulfite.

An example of a suitable chelating agent is tetrasodium EDTA.

An example of preservative booster includes pentylene glycol.

In one embodiment, the stabilizing step involves incubating the cell serum fraction in a mixture of at least one preservative, at least one chelating agent, at least one antioxidant, and at least one preservative efficacy booster to yield a stabilized cell serum fraction.

In another embodiment, the stabilizing step involves incubating the cell serum fraction in a mixture of at least one preservative and at least one antioxidant to yield a stabilized cell serum fraction.

In one embodiment of present invention, Serum-Derived Cosmetic Composition is *Nelumbo nucifera* (Sacred Lotus) Serum fraction (also known as *Nelumbo nucifera* extract, lotus serum fraction, Recentia® NN and Harmoniance™).

In another embodiment of present invention, Serum-Derived Cosmetic Composition is *Chamomilla recutita* (*Matricaria*) (German Chamomile) Flower Serum fraction (also known as chamomile flowers serum fraction, Recentia® CR-F, Recentia *Chamomilla recutita* Zeta Fraction).

The present invention also relates to a cosmetic care method including the topical application, on at least a portion of the skin of the body or face, of a *Nelumbo nucifera* (Sacred Lotus) serum fraction (it is also known as lotus serum fraction, Harmoniance™ and Recentia® NN) in a composition containing a physiologically acceptable medium, in order to mitigate adverse effects of sunlight on skin.

The present invention also relates to a cosmetic care method including the topical application, on at least a portion of the skin of the body or face, of a *Chamomilla recutita* (*Matricaria*) (German Chamomile) Flower Serum fraction (also known as chamomile flowers serum fraction, Recentia® CR-F, Recentia *Chamomilla recutita* Zeta Fraction) in a composition containing a physiologically acceptable medium, in order to mitigate adverse effects of sunlight on skin.

The compositions for implementation of the invention may in particular be in the form of an aqueous, hydroalcoholic or oily solution; and oil-in-water emulsion, a water-in-oil emulsion or multiple emulsions; they may also be in the form of suspensions, or powders, suitable for application on the skin, mucous membranes, lips and/or hair.

These compositions may be more or less fluid and have the appearance of a cream, a lotion, a milk, a serum, a pomade, a gel, a paste or a foam. They may also be in solid form such as a stick or be applied on the skin in the form of aerosol.

These compositions may also include any additive commonly used in the field of application envisaged, as well as the adjuvants necessary for their formulation, such as solvents, thickeners, diluents, antioxidants, coloring agents, sunscreens, self-tanning agents, pigments, fillers, preservatives, fragrances, odor absorbers, cosmetic or pharmaceutical active agents, essential oils, vitamins, essential fatty acids, surfactants, film-forming polymers, and so on.

In every case, a person skilled in the art will ensure that said adjuvants (excipients) as well as the proportions thereof are chosen so as not to interfere with the desired advantageous properties of the composition of the invention. These adjuvants may, for example, correspond to 0.01 to 20% of the total weight of the composition. When the composition of the invention is an emulsion, the fatty phase may represent 5 to 80% by weight and preferably 5 to 50% by weight with respect to the total weight of the composition. The emulsifiers and co-emulsifiers used in the composition will be chosen from those conventionally used in the field considered. For example, they may be used in a proportion ranging from 0.3 to 30% by weight, with respect to the total weight of the composition.

Advantageously, the composition capable of being used for the invention may include, in addition to the active agents according to the invention, at least one other active agent having effects that are similar and/or complementary to those of the invention. According to the invention, this active agent will be defined as an "additional active agent".

For example, the additional active agent(s) may be chosen from: sunscreen actives, anti-UV, anti-VIS, anti-IR, photo-stabilizers, anti-aging, toning, lightening, hydrating, draining, and microcirculation-promoting agents, pharmaceutical, exfoliating, scrubbing, extracellular matrix-stimulating, energy metabolism-activating, antibacterial, antifungal, calming, anti-free radical, and anti-acne agents, anti-inflammatory agents, anesthetics, warming agents, cooling agents and weight-loss agents.

Such additional agents may be chosen from the groups including: vitamin A and in particular retinoic acid, retinol, retinol propionate, retinol palmitate, vitamin B3 and more specifically niacinamide, tocopherol nicotinate, vitamin B5, vitamin B6, vitamin B12, vitamin C, in particular ascorbic acid, ascorbyl glucoside, ascorbyl tetrapalmitate, magnesium and sodium ascorbyl phosphate, vitamins E, F, H, K, PP, coenzyme Q10, metalloproteinase inhibitors, a TIMP activator, DHEA, precursors and derivatives thereof; amino acids such as arginine, ornithine, hydroxypropline, hydroxyproline dipalmate, palmitoylglycine, hydroxylysine, methionine and derivatives thereof, N-acyl amino acid compounds, natural or synthetic peptides, including di-, tri-, tetra-, penta- and hexapeptides and the lipophilic derivatives thereof, isomers and complexed with other species such as a metal ion (e.g. copper, zinc, manganese, magnesium, and others). For example, the peptides commercially known under the names MATRIXYL™, ARGIRELINE™, COLLAXYL™, PEPTIDE VINCI 02™, CHRONOGEN™, LAMINIXYL IS™, PEPTIDE Q10™, ATPeptide™, SURVIXYL IS™, NEOMATRIX™, plant-based peptide extracts such as extracts of soy, spelt, grapevine, rapeseed, linseed, rice, corn, pea, yeast extracts, Artemia Salina extracts, dehydroacetic acid (DHA), phytosterols of synthetic or natural origin, salicylic acid and derivatives thereof, alpha- and beta-hydroxyacids, amino sugars, glucosamine, D-glucosamine, N-acetyl-glucosamine, N-acetyl-D-glycosamine, mannosamine, N-acetyl mannosamine, galactosamine, N-acetyl galactosamine extracts of polyphenols, isoflavones, flavonoids, such as grape extracts, pine extracts and olive extracts, lipids such as ceramides or phospholipids, oils of animal origin, such as squalene or squalane; plant oils, such as sweet almond, copra, ricin, jojoba, olive, rapeseed, peanut, sunflower, wheat germ, corn germ, soy, cottonseed, alfalfa, poppy, winter squash, evening primrose, millet, barley, rye, safflower, passion fruit, hazelnut, palm, apricot seed, avocado, and calendula oil; ethoxylated plant oils, and shea butter, all UV screens and broad spectrum sunscreens.

The composition capable of being used according to the invention may be applied by any suitable route, in particular by external topical route, and the formulation of the compositions will be adapted by a person skilled in the art.

Advantageously, the compositions according to the invention are in a form suitable for topical application. These compositions must therefore contain a physiologically acceptable medium, i.e. compatible with the skin and skin appendages, and cover all cosmetic forms.

It is obvious that the invention concerns mammals in general, and more specifically human beings.

Specific embodiments of this cosmetic treatment method also result from the above description. Other advantages and features of the invention will be more apparent upon reading the examples provided for illustrative and non-limiting purposes.

EXAMPLES

The following examples are intended to illustrate particular embodiments of the present invention, but are by no means intended to limit the scope of the present invention.

Example 1

Figure 2:
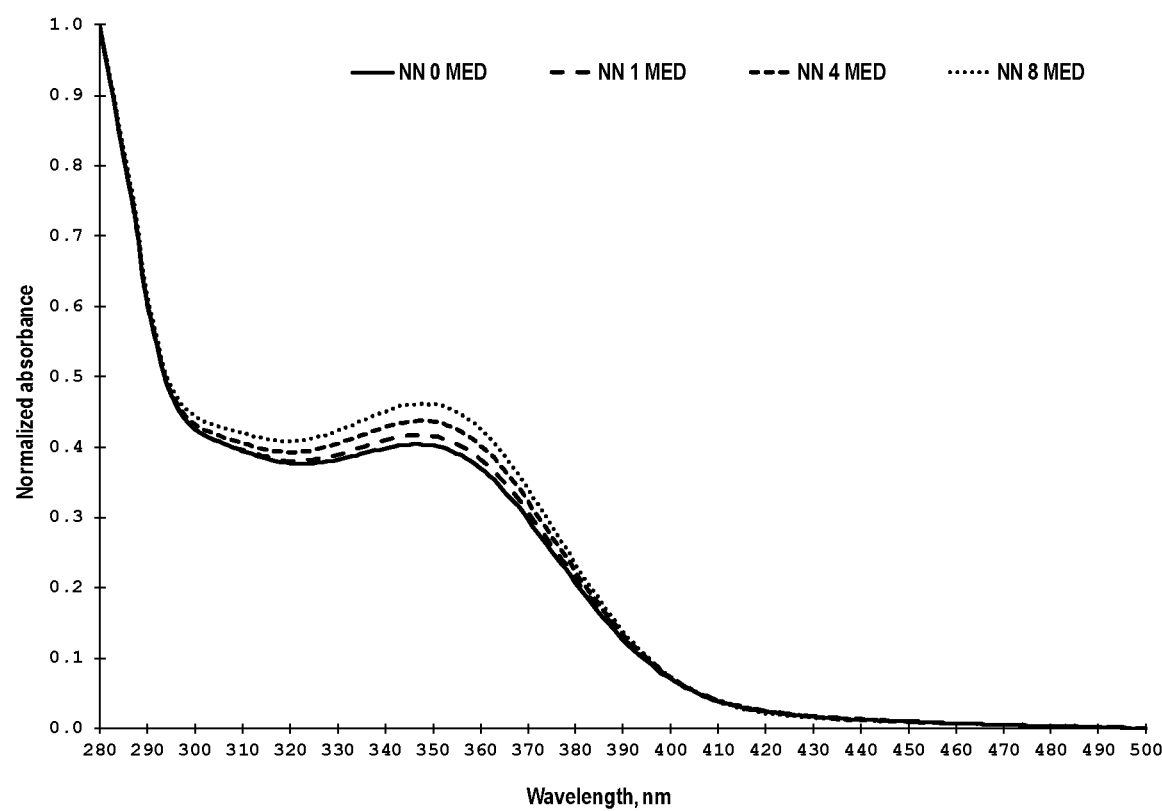
FIG. 2 shows normalized absorbance spectra of 5% *Nelumbo nucifera* (Sacred Lotus) serum fraction—before and after irradiation.
Figure 3:
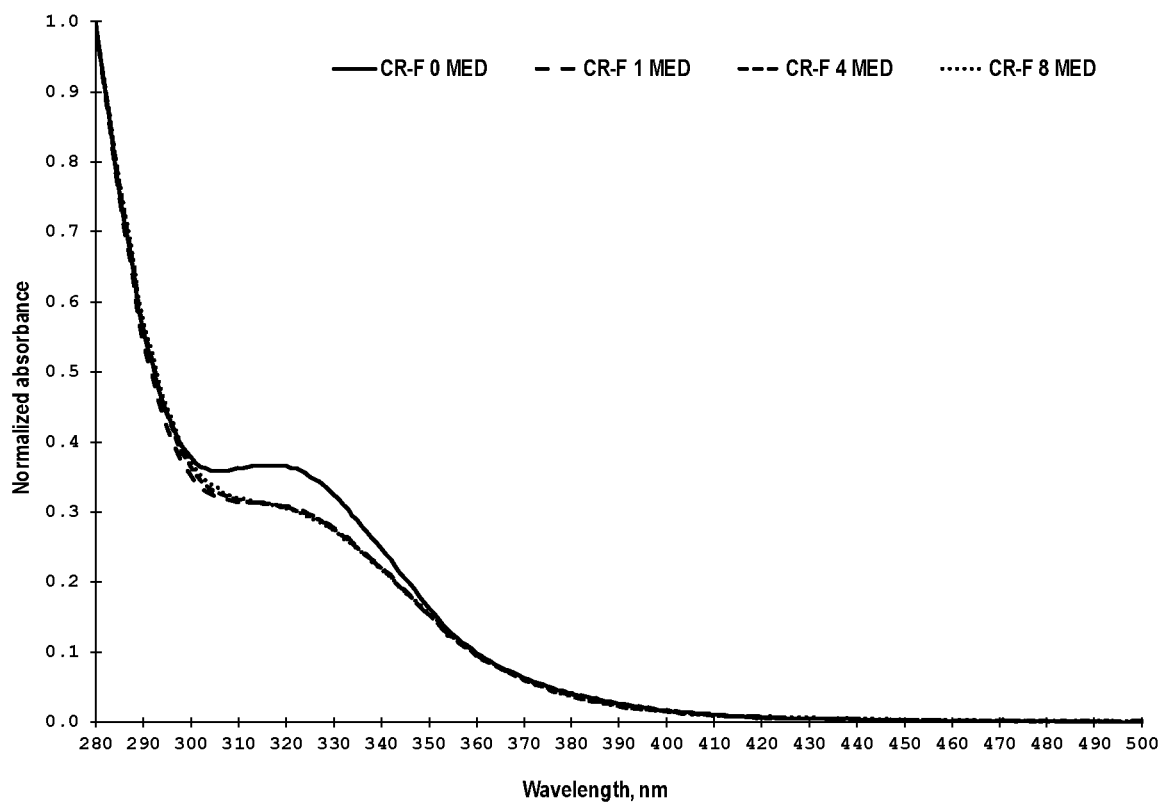
FIG. 3 shows normalized absorbance spectra of 5% *Chamomilla recutita* (*Matricaria*) (German Chamomile) Flower serum fraction—before and after irradiation.

Testing of *Nelumbo nucifera* (Sacred Lotus) and *Chamomilla recutita* (*Matricaria*) (German Chamomile) Flower Serum Fractions The description of analytical, cell culture based bioassays, enzymatic assays and in vitro assays used to evaluate *Nelumbo nucifera* (Sacred Lotus) serum fraction and *Chamomilla recutita* (German Chamomile) Flower serum fraction and relevant testing results are described below and in the Tables 1-8 and FIGS. 2-3.

Analytical methods used to determine compositions of *Nelumbo nucifera* (Sacred Lotus) serum fraction and *Chamomilla recutita* (German Chamomile) Flower serum fraction are as follows.

Total Soluble Sugars:

Total soluble sugars analyses in these serum fractions was based on colorimetry method described in: "Estimation of Carbohydrates in Plant Extracts" by Anthrone by Yemm and Willis, Biochem J.; 57(3): 508-514 (1954). The samples analyses were conducted with the following approach: a standard (two-sugar mixture) was made from a combination of ~200 ppm each of fructose and glucose, totaling 414 ppm of monosaccharide. Serial dilutions of this stock standard with water were made and 1 mL of each solution was reacted with 5 mL of ice cold 2000 ppm anthrone in 72% sulfuric acid. The reagents were heated to 100° C. for 10 minutes and a four-point calibration curve was created from the absorbance values of these solutions at 680 nm. Test sample was diluted in water to a 0.5% solution based on weight and the same reaction carried out. The absorbance of these solutions at 680 nm compared against the calibration curve was used to determine their total sugar concentrations. For samples and standards, a quartz 1 cm cuvette was used and a blank absorbance value was taken with pure water.

Total Phenolic Compound Content:

Total phenolic compound content in these serum fractions was determined by the method described in: "Estimation of total phenolic content and other oxidation substrates in plant tissues using Folin-Ciocalteu reagent" by Ainsworth and Gillespie, Nature Protocols; 2: 875-877 (2007). Colorimetric total phenolics assay described in this paper utilizes Folin-Ciocalteu (F-C) reagent. The F-C assay relies on the transfer of electrons in alkaline medium from phenolic compounds to phosphomolybdic/phosphotungstic acid complexes, which are determined spectroscopically at 765 nm. The samples analyses were conducted according to this method—starting with step 5. The volumes in steps 5, 6 and 7 were doubled to yield sufficient volume for a disposable reduced volume cuvette. Each sample for measurement was prepared in an individual cuvette. In step 6, F-C reagent addition, the sample and reagent were mixed and allowed to stand for ~10 minutes before carbonate addition. At the end of two hours, the samples and standard (chlorogenic acid) solutions were measured at 765 nm versus air; total phenolic content in the samples was calculated using chlorogenic acid (standard) calibration curve.

Analytical data and ranges for *Nelumbo nucifera* (Sacred Lotus) Serum Fraction* is shown in Table 1 below:

TABLE 1

| | | |
|---|---|---|
| Dry matter (plant based non- volatile solids) | 6.59-6.78 (%) w/w | |
| Total soluble sugars | 2.29-2.54 (%) w/w | ~33.8-38.5% of plant based non-volatile solids (extractives) |
| Total phenolic compounds | 1.33-1.58 (%) w/w | ~19.6-23.9% of plant based non-volatile solids (extractives) |

* *Nelumbo nucifera* (Sacred Lotus) Serum fraction was analyzed "as is".

Analytical data and ranges for *Chamomilla recutita* (German Chamomile) Flower Serum fraction* is shown in Table 2 below:

TABLE 2

| | | |
|---|---|---|
| Dry matter (plant based non- volatile solids) | 3.30-4.70% w/w | |
| Total soluble sugars | ~1.33-1.89 (%) w/w | ~40.3-57.2% of plant based non-volatile solids (extractives) |
| Total phenolic compounds | ~0.10-0.15 (%) w/w | ~3.0-4.5% of plant based non-volatile solids (extractives) |

* *Chamomilla recutita* (German Chamomile) Flower Serum fraction was analyzed "as is".

Safety and toxicological profile of *Nelumbo nucifera* (Sacred Lotus) Serum fraction was assessed using well described methods. *Nelumbo nucifera* (Sacred Lotus) Serum fraction was tested at the concentrations up to 100% (non-diluted). It was found that it is: Not irritant (demonstrated in skin Irritation studies: reconstructed human epidermis); Very well tolerated (in human 48 hrs patch test on 10 volunteers); Practically not irritant (Eye Irritation studies Het-Cam test); Not irritant (Reconstituted Human Corneal Epithelial (RHCE) Long exposure-time treatment test); In addition, it demonstrated no phototoxic potential in phototoxicity study (Neutral Red Uptake phototoxicity Test on 3T3 cells, 3T3 NRUPT in vitro method); non-sensitizer (Human Repeat Insult Patch at 10%, N>200), and non-genotoxic ("Ames" bacterial reverse mutation).

Safety and toxicological profile of *Chamomilla recutita* (German Chamomile) Flower Serum fraction was assessed using well described methods. *Chamomilla recutita* (German Chamomile) Flower Serum fraction was tested at the concentrations up to 100% (non-diluted). It was found that it is: Not irritant (demonstrated in skin Irritation studies: reconstructed human epidermis); Very well tolerated (in human 48 hrs patch test on 10 volunteers); Practically not irritant (Eye Irritation studies Het-Cam test); Not irritant (Reconstituted Human Corneal Epithelial (RHCE) Long exposure-time treatment test); In addition, it demonstrated no phototoxic potential in phototoxicity study (Neutral Red Uptake phototoxicity Test on 3T3 cells, 3T3 NRUPT in vitro method).

Cell culture based bioassays utilize cultured epidermal keratinocytes from human skin (Human Epidermal Keratinocytes, HEK) that release numerous signaling substances such as cytokines (IL-6), chemokines (IL-8) and prostaglandins ($PGE_2$) in response to sunlight. Amounts of these mediators are measured via techniques such as Enzyme-Linked Immunosorbent Assay (ELISA). It is known that bioactive ingredients capable of reducing HEK release of these inflammatory mediators may help control the signs of irritation and inflammation in human skin resulting from sun exposure. Normal human adult epidermal keratinocytes (HEK) and all cell culture supplies were obtained from Life Technologies Co. (Carlsbad, Calif., USA). The cells were grown and then maintained in keratinocyte basal medium 154 (M154) with added human keratinocyte growth supplements (HKGS) at 37° C. in an atmosphere of 5% $CO_2$ and used between passages 2 to 4. For the experiments, HEK cells were trypsinized, seeded in 96-well plates, and grown to ~80% confluence. The cells were washed once, and M154 was replaced with PBS. Both the washing and the replacement were done with PBS, to remove light-absorbing components of M154. The 96-well plate containing HEK was then covered with UV-transparent 1 mm quartz sheet, placed on white underlay atop controlled Peltier-cooled surface maintaining room temperature, and irradiated with a dose of 20 $J/cm^2$ of artificially produced full spectrum sunlight at dose rate of about 1100 $W/m^2$, as measured via pyranometer through same quartz cover. PBS was then removed and replaced with M154, and cells were incubated with test articles and/or controls for 16 hours. Irradiation equipment was obtained from Solar Light Company, Glenside, Pa. and included Solar Simulator LS1000-6R-002 in Airmass 1.5 configuration using plain mirror; XPS1000 precision current source, and PMA2144 Pyranometer. Identical manipulations, with exception of presence of sunlight, were carried out with HEK serving as unstressed controls. After incubation, HEK cell supernatants were collected. Quantikine® ELISA kits (R&D Systems Inc, Minneapolis, Minn.) were used to quantify interleukins in the supernatants. IL-8 was quantified by Human CXCL/IL-8 Immunoassay kit (Catalog #D8000C), IL-6 was quantified by Human IL-6 Immunoassay kit (Catalog #D6050); and $PGE_2$ was quantified using Parameter™ Prostaglandin $E_2$ Assay (Catalog #KGE004B). $IC_{50}$ (concentration of test article necessary to reduce interleukin or prostaglandin levels to 50%, with samples from non-irradiated cells considered as 0% and from irradiated cells considered as 100%) values were calculated by sigmoidal curve fitting with SigmaPlot 10.0 (Systat Software). Lower $IC_{50}$ values indicate higher potency and a degree of efficacy.

ORAC (Oxygen Radical Absorbance Capacity) was determined by ORAC testing using the method described in "Performing Oxygen Radical Absorbance Capacity (ORAC) Assays with Synergy HT Multi-Detection Microplate Reader" Application Note from BioTek [ORAC Assay Application Note—published in biotek website] which was modified for use with Synergy 2 microplate reader from BioTek instruments Inc (Winooski, Vt.). In this assay, AAPH (2,2'-azobis 2-amino-propane) generates reactive oxygen species which damage the fluorescent probe (sodium fluorescein). Antioxidants such as (R)-Trolox methyl ether prevent or slow this damage, and their effects can be quantified by fluorescence measurements. Fluorescence readings were continuously taken for 2 hours at 37° C. with excitation wavelength set at 485 nm and emission wavelength set at 528 nm, with reaction volume of 200 µl, AAPH concentration of 55 mM, sodium fluorescein concentration of 133 µM, and (R)-Trolox methyl ether concentration range between 80 µM and 2 µM. Sodium fluorescein (Fluka 46960), AAPH (Sigma 440914) and (R)-Trolox methyl ether (Fluka 93509) were obtained from Sigma-Aldrich (St, Louis, Mo.). AUC (Area Under Curve) values were calculated as sum of proportions (current fluorescence reading for the well divided by first fluorescence reading for the well). Average of AUC values of wells with deionized water was subtracted from AUC of wells with (R)-Trolox methyl ether and wells with test articles to obtain AUC corresponding to preservation of fluorescence by antioxidants. A calibration curve was generated as function of a wells' antioxidant-related AUC showing (R)-Trolox methyl ether weight-equivalent ORAC activity. ORAC activity for test articles was then calculated as 1 g. test article, necessary to achieve antioxidant effect equal to one produced by 1 mg (R)-Trolox methyl ether, with lower numbers indicating higher ORAC activity.

DPPH (2,2-Diphenyl-1-Picrylhydrazyl) assay. Free radical is a molecule or an atom with one or more unpaired valence shell electrons. Such substances are often but not always unstable, chemically transient and highly reactive. Free radicals can be produced by many processes including combustion, irradiation by sunlight, and normal metabolism—especially involving cellular respiration, immune response and inflammation processes. In biological systems, free radicals most commonly involve oxygen metabolism and reactive oxygen species. High reactivity of free radicals can let them damage biological molecules. In cases where products of such reactions are free radicals themselves, this can lead to a cascade of damage. Such damage can trigger inflammatory responses, potentially leading to harmful self-sustaining loops. This is particularly relevant in the human skin, as the organ most exposed to free radical generating environmental stresses. Therefore, a method to measure ability of a substance to quench or scavenge free radicals could be useful in determining what substances are effective antioxidants and could help mitigate and prevent signs of skin damage related to free radicals and processes they trigger. One common approach involves is the use of a stable free radical which is intensely colored due to electron delocalization while in free radical state, and loses that color if quenched. DPPH is a stable organic free radical very suitable for use in colorimetric assays as its radical form is violet-black in solid form and violet in its methanol solution, while quenched form is pale yellow in solution. This change can be measured as decrease in absorbance at 515 nm wavelength. The kinetics of this decrease also may provide qualitative judgment about the speed of the free radical scavenging by test articles. DPPH (2,2-Diphenyl-1-Picrylhydrazyl) free radical scavenging activity was determined by a kinetic colorimetric assay adapted for use with glass-coated polypropylene 96-well microtiter plates (catalog number 400 062) from SUN-SRi (Rockwood, Tenn.) and Synergy 2 microplate reader from BioTek Instruments Inc (Winooski, Vt.). Absorbance was measured at 515 nm wavelength. Reaction volume in each microplate well was 200 with initial concentration of DPPH equal to 114 µM. DPPH (Sigma D9132) was obtained from Sigma-Aldrich (St. Louis, Mo.). Stoichiometry of the reaction was calculated and expressed as 1 g test article necessary to quench 1 mg DPPH, with lower numbers indicating higher activity. This method was adapted from procedure described in the article "Use of a free radical method to evaluate antioxidant activity" by W. Brand-Williams et al, published in LWT—Food Science and Technology, Volume 28, Issue 1, 1995, pp 25-30.

Evaluation of *Nelumbo nucifera* (Sacred Lotus) serum fraction and *Chamomilla recutita* (German Chamomile) Flower serum fraction in DPPH assay. 5% v/v dilutions of *Nelumbo nucifera* (Sacred Lotus) serum fraction and *Chamomilla recutita* (German Chamomile) Flower serum fraction were prepared in deionized water immediately prior to testing. 70 microliter aliquots (amount sufficient for forming a meniscus in the test setup) of these dilutions, as well as deionized water as a blank, were placed in wells of a quartz 96-well microtiter plate (clear bottom, black sides, obtained from Hellma Analytics). The plate was covered with 1 millimeter thick quartz sheet. The covered plate was placed on white underlay atop Peltier-cooled surface (Torrey Pines Scientific heating/chilling dry bath/shaker with microplate holder attachment). Peltier cooling was set to 15 degrees Celsius. The plate was irradiated using a solar simulator (LS-1000 from SolarLight) with filter and mirror configuration corresponding to airmass 1.5. Prior to irradiation of the samples, time corresponding to 1 Minimal Erythemal Dose (MED) for solar simulator light passing through the 1 millimeter quartz sheet was measured using a data-logging radiometer with erythema detector (PMA2100 and 2101 respectively, both from SolarLight). The quartz plate with samples was irradiated for a time corresponding to exposure to 4 MED.

*Nelumbo nucifera* (Sacred Lotus) serum fraction and *Chamomilla recutita* (German Chamomile) Flower serum fraction—before and after irradiation—were tested in DPPH quenching assay as described above, in concentrations ranging about 10% v/v to about 0.2% v/v in reaction volume, with deionized water used as diluent.

Both, *Nelumbo nucifera* (Sacred Lotus) serum fraction and *Chamomilla recutita* (German Chamomile) Flower serum fraction maintained more than 95% of their initial DPPH quenching capacities after 4 MED exposure delivered by full spectrum simulated sunlight—as shown in Tables 3 and 4.

TABLE 3

DPPH activity of *Nelumbo nucifera* (Sacred Lotus) Serum fraction before and after irradiation

| | mg/g DPPH | | |
|---|---|---|---|
| | 0 MED | 4 MED | % Reduction |
| *Nelumbo nucifera* (Sacred Lotus) Serum fraction diluted to 5% v/v with Deionized Water | 3.2210 | 3.1020 | 3.7 |

TABLE 4

DPPH activity of *Chamomilla recutita* (German Chamomile)
Flower serum fraction before and after irradiation

| | mg/g DPPH | | |
|---|---|---|---|
| | 0 MED | 4 MED | % Reduction |
| *Chamomilla recutita* (German Chamomile) Flower serum fraction diluted to 5% v/v with Deionized Water | 0.0685 | 0.0656 | 4.2 |

Critical Wavelength (CW), nm was determined according to FDA, Final Rule 2011. Absorbance of a 0.75 mg/square cm film is measured between 290 nm and 400 nm, after 4 MED pre-irradiation. CW defined as the wavelength at which the integral of the spectral absorbance curve reaches 90% of the integral from 290 to 400 nm.

Absorbance spectra and photostability evaluations of *Nelumbo nucifera* (Sacred Lotus) serum fraction and *Chamomilla recutita* (German Chamomile) Flower serum fraction: 5% v/v dilutions of *Nelumbo nucifera* (Sacred Lotus) Serum fraction and *Chamomilla recutita* (German Chamomile) Flower Serum fraction were prepared in deionized water immediately prior to testing. 70 microliter aliquots (amount sufficient for forming a meniscus in the test setup) of these dilutions, as well as deionized water as a blank, were placed in wells of a quartz 96-well microtiter plate (clear bottom, black sides, obtained from Hellma Analytics). The plate was covered with 1 millimeter thick quartz sheet. The covered plate was placed on white underlay atop Peltier-cooled surface (Torrey Pines Scientific heating/chilling dry bath/shaker with microplate holder attachment). Peltier cooling was set to 15 degrees Celsius. Plate holder temperature was 18 C. The plate was irradiated using a solar simulator (LS-1000 from SolarLight) with filter and mirror configuration corresponding to airmass 1.5. Prior to irradiation of the samples, time corresponding to 1 Minimal Erythemal Dose (MED) for solar simulator light passing through the 1 millimeter quartz sheet was measured using a datalogging radiometer with erythema detector (PMA2100 and 2101 respectively, both from SolarLight). The quartz plate with samples was irradiated for total exposures corresponding to 1, 4, and 8 MEDs. 1 MED was 14 min 25 sec for this test. Top of plate reached maximum of about 36 deg. C. during irradiation. Absorbance spectra of the microtiter plate contents at wavelengths from 280 nanometers to 500 nanometers were obtained using BioTek Synergy 2 microplate reader before irradiation, as well as after 1; 4, and 8 MED total exposures.

Resulting absorbance curves of wells with deionized water were subtracted from absorbance curves for the diluted serum fractions. These blank-subtracted curves were then normalized for clearer qualitative comparison of shapes and proportions. The normalization was a rescaling which considered the maximum absorbance of a curve as 1, and minimum absorbance of a curve as 0. The different nature of these decreases is clearly shown by normalized absorbance curves.

UVA-UVB Ratios of *Nelumbo nucifera* (Sacred Lotus) serum fraction and *Chamomilla recutita* (German Chamomile) Flower serum fraction were determined based on the normalized absorbance curves measured between 290 nm and 400 nm—before and after irradiation. The ratio of areas under the curve between 290-320 (UVB region) was compared with the area under the curve between 320 nm and 400 nm (UVA region). UVA/UVB ratio is the parameter of choice used by the industry to determine the protection potential and photostability of various ingredients, sunscreen actives and finished goods.

The normalized absorbance spectra of 5% *Nelumbo nucifera* (Sacred Lotus) serum fraction (FIG. 2) show that increasing exposure to simulated full spectrum sunlight causes proportionally higher attenuation from about 310 nm to about 380 nm wavelengths, with most notable difference being the peak at about 350 nanometers. Beneficial changes in UVA/UVB ratios after irradiation (shown in Table 5) correspond mainly to the increase of the absorbance in UVA1 (340 nm-400 nm) region.

TABLE 5

UVA/UVB Ratios of *Nelumbo nucifera* (Sacred Lotus)
Serum fraction before and after irradiation

| | 0 MED | 1 MED | 4 MED | 8 MED |
|---|---|---|---|---|
| UVA/UVB Ratio | 1.83 | 1.88 | 1.93 | 1.97 |

The normalized absorbance spectra of 5% *Chamomilla recutita* (German Chamomile) Flower serum fraction (FIG. 3) show that exposure to 1 MED causes proportionally lower absorbances from about 310 nm to about 340 nm. Further irradiation does not cause notable changes of absorbance spectra. Therefore, slight decrease in UVA/UVB ratios after irradiation (shown in Table 6) correspond mainly to the lowering of absorbance in UVA2 region (320 nm-340 nm) and partially in UVB region (290 nm-320 nm).

TABLE 6

UVA/UVB Ratios of *Chamomilla recutita* (German Chamomile)
Flower serum fraction before and after irradiation

| | 0 MED | 1 MED | 4 MED | 8 MED |
|---|---|---|---|---|
| UVA/UVB Ratio | 0.96 | 0.95 | 0.91 | 0.90 |

It was unexpectedly found that the *Nelumbo nucifera* (Sacred Lotus) serum fraction and *Chamomilla recutita* (German Chamomile) Flower serum fraction ingredients each have synergistic combinations of: beneficial spectral absorbance characteristics in UVA-UVB area in conjunction with potent biological activities demonstrated in various in vitro cell culture based bioassays associated with full spectrum sun exposure and relevant enzymatic models. Both ingredients maintained more than 95% of initial (pre-irradiation) DPPH quenching capacities after 4 MED exposure delivered by full spectrum simulated sunlight.

*Nelumbo nucifera* (Sacred Lotus) serum fraction demonstrated increased attenuation in UVA1 area as the radiation dose increased, which is an unusual, desirable and not anticipated property.

Activities of *Nelumbo nucifera* (Sacred Lotus) Serum fraction are summarized in Table 7 below.

TABLE 7

| Brief Description of the Assay | Results |
| --- | --- |
| Melanin synthesis inhibition in keratinocyte/ melanocyte tissue equivalent Melanoderm ™ tissue equivalents (from MatTek) incubated for 15 days with/without sample in cell culture medium. After incubation, tissue equivalents are photographed, lysed, and assayed for melanin content. Untreated tissues are compared to treated. | 5% serum fraction lowers melanin production by 30%, and results in lighter tissues |
| Inhibition of sun-induced IL8 (Interleukin 8) Human Epidermal Keratinocyte monolayer culture is exposed, or not, to 20 J/cm$^2$ of simulated full spectrum sunlight, and incubated for 16 hours with/without sample in cell culture medium. Cell culture supernatants are evaluated via ELISA. With unexposed controls considered as 0% IL8 and exposed as 100% IL8, IC$_{50}$ is sample concentration needed to reduce IL8 level by half. | IC$_{50}$ ≤ 0.005% |
| Inhibition of sun-induced PGE$_2$ (Prostaglandin E2) Human Epidermal Keratinocyte monolayer culture is exposed, or not, to 20 J/cm$^2$ of simulated full spectrum sunlight, and incubated for 16 hours with/without sample in cell culture medium. Cell culture supernatants are evaluated via ELISA. With unexposed controls considered as 0% PGE$_2$ and exposed as 100% PGE$_2$, IC$_{50}$ is sample concentration needed to reduce PGE$_2$ level by half. | IC$_{50}$ ≤ 0.05% |
| Elastase inhibition Human elastase cleaves a synthetic polypeptide labeled with dye moiety, releasing the dye and resulting in color development. Speed of reaction is measureable from absorbance curves over time. IC$_{50}$ is sample concentration needed to slow reaction by half. | IC$_{50}$ = 0.25% . . . 0.41% |
| MMP3 (Matrix Metalloproteinase-3) inhibition MMP3 cleaves a synthetic thiopeptide, producing a sulfhydryl group, which reacts with 5,5'-dithiobis (2-nitrobenzoic acid) resulting in color development. Endpoint or kinetic absorbance measurements allow determining cleavage speed. IC$_{50}$ is sample concentration needed to slow reaction by half. | IC$_{50}$ ≤ 0.03% |
| ORAC (Oxygen Radical Absorbance Capacity) Free radicals produced by generator substance degrade fluorescein. Antioxidants prevent degradation, with effect calculated from fluorescence intensity curves over time. Effect of sample is compared to calibration curve of an antioxidant standard. | 1 g (as supplied) has potency equal to ~30.6 mg of (R)-Trolox methyl ether |
| DPPH (2,2-diphenyl-1-picrylhydrazyl) quenching Stable artificial free radical changes color when quenched to non-radical form by an anti-oxidant. Measuring absorbance curves over time allows determination of speed and stoichiometry of quenching by sample. | 1 g (as supplied) quenches ~25.8-40.1 mg DPPH |
| Critical Wavelength, CW, nm (determined according to the FDA, 2011) | 385 nm |

Activities of *Chamomilla recutita* (German Chamomile) Flower Serum fraction are summarized in Table 8 below.

TABLE 8

| Brief Description of the Assay | Results |
| --- | --- |
| Inhibition of sun-induced IL8 (Interleukin 8) Human Epidermal Keratinocyte monolayer culture is exposed, or not, to 20 J/cm$^2$ of simulated full spectrum sunlight, and incubated for 16 hours with/without sample in cell culture medium. Cell culture supernatants are evaluated via ELISA. With unexposed controls considered as 0% IL8 and exposed as 100% IL8, IC$_{50}$ is sample concentration needed to reduce IL8 level by half. | IC$_{50}$ = 0.2% |
| Inhibition of sun-induced IL6 (Interleukin 6) Human Epidermal Keratinocyte monolayer culture is exposed, or not, to 20 J/cm$^2$ of simulated full spectrum sunlight, and incubated for 16 hours with/without sample in cell culture medium. Cell culture supernatants are evaluated via ELISA. With unexposed controls considered as 0% IL8 and exposed as 100% IL6, IC$_{50}$ is sample concentration needed to reduce IL6 level by half. | IC$_{50}$ = 0.12% |
| Elastase inhibition Human elastase cleaves a synthetic polypeptide labeled with dye moiety, releasing the dye and resulting in color development. Speed of reaction is measureable from absorbance curves over time. IC$_{50}$ is sample concentration needed to slow reaction by half. | IC$_{50}$ = 1.1% |
| ORAC (Oxygen Radical Absorbance Capacity) Free radicals produced by generator substance degrade fluorescein. Antioxidants prevent degradation, with effect calculated from fluorescence intensity curves over time. Effect of sample is compared to calibration curve of an antioxidant standard. | 1 g (as supplied) equals to 8 mg of (R)-Trolox methyl ether |
| DPPH (2,2-diphenyl-1-picrylhydrazyl) quenching Stable artificial free radical changes color when quenched to non-radical form by an anti-oxidant. Measuring absorbance curves over time allows determination of speed and stoichiometry of quenching by sample. | 1 g quenches ~2.8-3.3 mg DPPH |
| Critical Wavelength, CW, nm (determined according to the FDA, 2011) | 375 nm |

The experimental results suggest that ingredients of present invention provide multifunctional activities that work together to mitigate various adverse effects of full spectrum sunlight exposure on skin cells.

Example 2

Effect of *Nelumbo nucifera* (Sacred Lotus) Serum Fraction on Wrinkle Appearance Compared to Placebo in Formula Objective:

The objective of this experimental was to study the effect of the *Nelumbo nucifera* (Sacred Lotus) Serum Fraction (also referred to herein as Harmoniance™) on wrinkle appearance.

Methodology:

This was a comparative double-blind study against a placebo, conducted on the face of 20 volunteers for an eight-week period. Principal assessment criterion was based on the skin topography measurement by fringe projection 3D imaging (DermaTOP*).

Experimental Protocol:

Every side of the face received either the biofunctional product formulated at 0.5% in a skin care formula or its placebo. Before that, a conditioning phase was performed; the placebo cream in this study was used as conditioning products, which were distributed to the subjects 8 days before the DO visit. The first application took place at the laboratory after measurements of DO. The following ones were done by the subjects, twice a day, morning and evening, up to the end of the test. The volunteers stopped the cream application the evening before the visit day D56.

Results:

After four weeks of applications, different wrinkle parameters (the volume and the area) as well as skin micro relief (Rz) significantly decreased for the biofunctional treated sides compared to the placebo treated sides and kept decreased after eight weeks of applications.

Moreover, after eight weeks of applications, we observed a significant decrease of the number of wrinkles for the sides treated with 0.5% Harmoniance containing-creams compared to the placebo treated sides.

Provided below in Tables 9-12 is data with respect to wrinkle appearance treatment efficiency of the *Nelumbo nucifera* (Sacred Lotus) Serum Fraction compared to placebo.

Number of Wrinkle Measurements

Table 9 illustrates measurements of the number of wrinkles by fringe projection, difference between DX and D0, for the 0.5% Harmoniance treated sides and placebo treated sides.

TABLE 9

| Treated sides | Time | Mean | sem | p | % of change | % of improved volunteers |
|---|---|---|---|---|---|---|
| Placebo | D28–D0 | −0.22 | 0.62 | 0.51$^{ns}$ | | |
| 0.5% Harmoniance | | −0.22 | 0.59 | | | |
| Placebo | D56–D0 | −0.06 | 0.55 | 0.0088** | −20.26% | 66.67% (12/18) |
| 0.5% Harmoniance | | −1.78 | 0.67 | | | |

DX being D28 or D56.
$^{ns}$not significant;
**very significant with Student's t-test or Wilcoxon test depending on whether the data followed a normal distribution or not;
mean +/− sem n = 18.
% of change = 100
*$[(D56_{Harmoniance} - D0_{Harmoniance}) - (D56_{Placebo} - D0_{Placebo})]/((D0_{Harmoniance} + D0_{Placebo})/2)$.

Volume of Wrinkle Measurements

Table 10 illustrates measurements of the volume of wrinkles (mm$^3$) by fringe projection, difference between DX and D0, for the 0.5% Harmoniance treated sides and placebo treated sides.

TABLE 10

| Treated sides | Time | Mean (mm$^3$) | sem | p | % of change | % of improved volunteers |
|---|---|---|---|---|---|---|
| Placebo | D28–D0 | 0.03 | 0.11 | 0.0247* | −13.72% | 61.11% (11/18) |
| 0.5% Harmoniance | | −0.15 | 0.1 | | | |
| Placebo | D56–D0 | −0.01 | 0.1 | 0.0406* | −11.68% | 66.67% (12/18) |
| 0.5% Harmoniance | | −0.17 | 0.07 | | | |

DX being D28 or D56.
*significant with Student's t-test or Wilcoxon test depending on whether the data followed a normal distribution or not;
mean +/− sem n = 18.
% of change = 100
*$[(DX_{Harmoniance} - D0_{Harmoniance}) - (DX_{Placebo} - D0_{Placebo})]/((D0_{Harmoniance} + D0_{Placebo})/2)$.

Area of Wrinkle Measurements

Table 11 illustrates measurements of the area of wrinkles (mm$^2$) by fringe projection, difference between DX and D0, for the 0.5% Harmoniance treated sides and placebo treated sides.

TABLE 11

| Treated sides | Time | Mean (mm$^2$) | sem | p | % of change | % of improved volunteers |
|---|---|---|---|---|---|---|
| Placebo | D28–D0 | 1.64 | 2.19 | 0.0256* | −16.77% | 61.11% (11/18) |
| 0.5% Harmoniance | | −1.99 | 1.34 | | | |

TABLE 11-continued

| Treated sides | Time | Mean (mm²) | sem | p | % of change | % of improved volunteers |
|---|---|---|---|---|---|---|
| Placebo | D56-D0 | 1.55 | 2.2 | 0.0152** | -21.67% | 72.22% (13/18) |
| 0.5% Harmoniance | | -3.14 | 1.5 | | | |

DX being D28 or D56.
*significant with Student's t-test or Wilcoxon test depending on whether the data followed a normal distribution or not;
mean +/- sem n = 18.
% of change = 100
*[($DX_{Harmoniance} - D0_{Harmoniance}) - (DX_{Placebo} - D0_{Placebo})$]/(($D0_{Harmoniance} + D0_{Placebo}$)/2).

Rz Measurements

Table 12 illustrates measurements of Rz parameters (mm) by fringe projection, difference between DX and D0, for the 0.5% Harmoniance treated sides and placebo treated sides.

TABLE 12

| Treated sides | Time | Mean (mm) | sem | p | % of change | % of improved volunteers |
|---|---|---|---|---|---|---|
| Placebo | D28-D0 | 0.0036 | 0.0054 | 0.0124* | -6.90% | 72.22% (13/18) |
| 0.5% Harmoniance | | -0.009 | 0.0053 | | | |
| Placebo | D56-D0 | -0.0042 | 0.005 | 0.0243* | -4.40% | 66.67% (13/18) |
| 0.5% Harmoniance | | -0.0122 | 0.0035 | | | |

DX being D28 or D56.
*significant with Student's t-test or Wilcoxon test depending on whether the data followed a normal distribution or not;
mean +/- sem n = 18.
% of change = 100
*[($DX_{Harmoniance} - D0_{Harmoniance}) - (DX_{Placebo} - D0_{Placebo})$]/(($D0_{Harmoniance} + D0_{Placebo}$)/2).

General Conclusion:

The purpose of the double blind study was to evaluate in vivo the effect of a treatment with Harmoniance-containing creams on wrinkle appearance compared to placebo cream.

The effect was first confirmed by a significant decreased of the number of wrinkles as well as their volume and area.

Moreover, the skin micro relief (Rz) significantly decreased after four weeks of applications with 0.5% Harmoniance suggesting a smoother skin.

The smoothening of the skin and the reduction of wrinkles were observed on color pictures of the crow's feet and on skin topography pictures.

Under the present conditions, these results confirmed the efficiency of 0.5% Harmoniance to reduce wrinkle appearance.

Example 3

Effect of *Nelumbo nucifera* (Sacred Lotus) Serum Fraction on Skin Hydration Compared to Placebo in Formula Objective:

The objective of this experimental was to study the effect of the *Nelumbo nucifera* (Sacred Lotus) Serum Fraction (also referred to herein as Harmoniance™) on skin hydration.

Methodology:

This was a comparative double-blind study against a placebo, conducted on the forearms of 20 volunteers for a six-hour period. Principal assessment criterion is based on skin hydration measurement.

Experimental Protocol:

Two areas of 30 cm², facing each other, were determined on the forearm for measurements and applications of either the biofunctional product formulated at 0.5% in a skin care formula or its placebo. A third area was determined below one of these areas for the untreated condition. The only application took place at the laboratory after measurements of T0.

Results:

We noticed a highly significant improvement of skin hydration 3 h and 6 h after application of the Harmoniance-containing creams compared to the placebo creams.

Provided below in Tables 13-15 is data with respect to skin hydration treatment efficiency of the *Nelumbo nucifera* (Sacred Lotus) Serum Fraction compared to placebo.

Skin Hydration Measurements

Hydration measurements were performed with the Corneometer* CM 825 (Courage & Khazaka*) using the method of capacitance.

Table 13 illustrates hydration measurements (capacitance, AU), difference between TX and T0, for the 0.5% Harmoniance treated sides and placebo treated sides.

TABLE 13

| Treated sides | Time | Mean (AU) | sem | p | % of change | % of improved volunteers |
|---|---|---|---|---|---|---|
| Placebo | T3h–T0 | 5.77 | 1.13 | 0.0006*** | +13.92% | 85% (17/20) |
| 0.5% Harmoniance | | 9.70 | 0.82 | | | |
| Placebo | T6h–T0 | 5 | 0.92 | 0.0004*** | +14.50% | 90% (18/20) |
| 0.5% Harmoniance | | 9.1 | 0.92 | | | |

TX being T3h or T6h.
***highly significant with Student's t-test or Wilcoxon test depending on whether the data followed a normal distribution or not;
mean +/− sem, n = 20.
% of change = 100
*[(TX$_{Harmoniance}$ − T0$_{Harmoniance}$) − (TX$_{Placebo}$ − T0$_{Placebo}$)]/((T0$_{Harmoniance}$ + T0$_{Placebo}$)/2).

We noticed a highly significant improvement of skin hydration 3 h and 6 h after application with the Harmoniance-containing creams compared to the placebo creams.

Transepidermal Water Loss

The Trans epidermal water loss (TEWL) was measured with the AquaFlux* AF200 (Biox*) which is a condenser-chamber (closed chamber) measurement method. This closed-chamber design eliminates disturbance of measurements by external air movements.

Due to a technical issue during the measurements, at T6 h, the results were given on 16 volunteers for this time.

Table 14 illustrates TEWL measurements (g/m$^2$ h), difference between TX and T0, for the 0.5% Harmoniance treated sides and placebo treated sides.

TABLE 14

| Treated sides | Time | Mean (g/m$^2$h) | sem | p | % of change | % of improved volunteers |
|---|---|---|---|---|---|---|
| Placebo | T3h–T0 | −0.93 | 0.22 | 0.0001*** | −7.55% | 90% (18/20) |
| 0.5% Harmoniance | | −1.80 | 0.26 | | | |
| Placebo | T6h–T0 | −0.71 | 0.17 | <0.0001*** | −7.76% | 87.5% (14/16) |
| 0.5% Harmoniance | | −1.60 | 0.20 | | | |

TX being T3h or T6h.
***highly significant with Student's t-test or Wilcoxon test depending on whether the data followed a normal distribution or not;
mean +/− sem, n = 20 at T3h and n = 16 at T6h.
% of change = 100
*[(TX$_{Harmoniance}$ − T0$_{Harmoniance}$) − (TX$_{Placebo}$ − T0$_{Placebo}$)]/((T0$_{Harmoniance}$ + T0$_{Placebo}$)/2).

A highly significant reduction of the TEWL was observed at 3 h and 6 h after application.

Skin Softness Measurements

Softness measurements were performed with the Frictiometer* FR 700 (Courage & Khazaka*).

Table 15 illustrates softness measurements (AU), difference between TX and T0, for the 0.5% Harmoniance treated sides and placebo treated sides.

TABLE 15

| Treated sides | Time | Mean (AU) | sem | p | % of change | % of improved volunteers |
|---|---|---|---|---|---|---|
| Placebo | T3h–T0 | 19.82 | 2.11 | 0.0002*** | +25.73% | 90% (18/20) |
| 0.5% Harmoniance | | 26.12 | 2.53 | | | |
| Placebo | T6h–T0 | 16.58 | 2.71 | 0.0017*** | +25.64% | 85% (17/20) |
| 0.5% Harmoniance | | 22.86 | 2.86 | | | |

TX being T3h or T6h.
***highly significant with Student's t-test or Wilcoxon test depending on whether the data followed a normal distribution or not;
mean +/− sem, n = 20.
% of change = 100
*[(TX$_{Harmoniance}$ − T0$_{Harmoniance}$) − (TX$_{Placebo}$ − T0$_{Placebo}$)]/((T0$_{Harmoniance}$ + T0$_{Placebo}$)/2).

A highly significant improvement of skin softness was observed at 3 h and 6 h after application.

General Conclusion:

The purpose of the double blind study was to evaluate in vivo the effect of a treatment with Harmoniance-containing creams on skin hydration.

The effect was first confirmed by a significant increase of the hydration of the skin after one single application.

Moreover, this improvement was characterized by a significant reduction of the TEWL indicating that Harmoniance at 0.5% may restore skin barrier function.

Measurements with the frictiometer pointed out the enhancement of the skin softness after application of Harmoniance-containing creams.

Under the present conditions, these results confirmed the efficiency of 0.5% Harmoniance to promote skin hydration.

Example 4

Effect of *Nelumbo nucifera* (Sacred Lotus) Serum Fraction on Cultured Cells and Normal Human Skin Biopsies Objective: In the present study, we evaluated in vitro and ex vivo, the effects of *Nelumbo nucifera* (Sacred Lotus) Serum Fraction (also referred to herein as Harmoniance™) on parameters implicated in 4 different axes: skin hydration and barrier function, skin laxity, drainage and skin pigmentation.

A. Hyaluronic Acid Fluorescent Staining in Skin Biopsies

Skin Biopsies:

Normal human skin came from a plastic surgery intervention on the breast of a 26-year-old female. Skin biopsies were obtained with a 6 mm diameter punch (pfm medical). They were cultivated on culture medium containing 50% of DMEM 1 g/L glucose (Lonza) and 50% of Ham's-F12 (Lonza) supplemented with 10% of FBS (Lonza), 2 mM of L-glutamine (Lonza) and 100 µg/mL of Primocin* (InvivoGen). Skin biopsies were maintained at 37° C. in a humidified atmosphere containing 5% of $CO_2$.

Additional experiments were performed on the breast skin of a 53 year-old and on the arm skin of a 64 year-old female donors.

Reagents:

Biotinylated hyaluronic acid binding protein (bHABP) was purchased from Coger and streptavidin—Alexa Fluor* 488 conjugate, from Invitrogen.

Principle:

Hyaluronic acid glycosaminoglycan is detected using the specific, biotinylated, binding protein: bHABP. The recognition of biotin by a streptavidin conjugated to a fluorochrome allows an examination under a fluorescence microscope.

Treatments:

Skin biopsies were treated, in duplicate, with PBS (Lonza) in placebo condition or with Harmoniance at 0.5% or 1%, twice a day, for 48 hours. 20 µL of solutions were applied on the top of the biopsies.

Biopsy Preparation:

To allow preservation and section of skin, tissues were fixed for 4 hours in buffered 10% formalin. Samples were transferred to baths with ethanol progressively concentrated to remove water, then followed by two baths of xylene to remove the alcohol, and finally embedded in molten paraffin wax. Embedded skin biopsies were then cut with a microtome (Shandon) into 4 µm thick sections and placed on Superfrost Plus* slides (Thermo Scientific).

Protocol:

Sections were deparaffinized and rehydrated with several successive xylene, alcohol and water baths. After a PBS wash, bHABP, diluted at 1/400, was applied and slides were incubated for 2 hours, under agitation, at room temperature, in a damp room. After having rinsed slides with PBS, the streptavidin, Alexa Fluor* 488 conjugate, diluted at 1/1000 was applied for 1 hour, in the dark, under agitation, at room temperature, in a damp room. Finally, sections were stained with 4',6'-diamidino-2-phenylindole (DAPI, Molecular Probes*) at 0.3 µM for 5 minutes and mounted in Fluoromount-G* (Electron Microscopy Sciences). Detection was managed and examined using a Zeiss Axiovert 200M microscope with a 20× objective. Photos were taken with a Qimaging* EXI blue camera coupled to Volocity* acquisition software (Improvision).

Image Quantification:

Three photos per condition were analyzed with Volocity* image analysis software (Improvision), which allows to select the interesting zone thanks to the fluorescence intensity. The results obtained were the sum of green pixel intensities in the selected zone. Finally, for each photo, the sum obtained was adjusted by considering the area of the examined epidermis and dermis zones.

Statistical Analyses:

Statistical analyses were performed using JMP* 11 software (SAS) and Student's t test for independent samples with one-tailed direction of rejection. $p \leq 0.05$ were considered as significant, $p \leq 0.01$ as very significant and $p \leq 0.005$ as highly significant.

Figure 4:
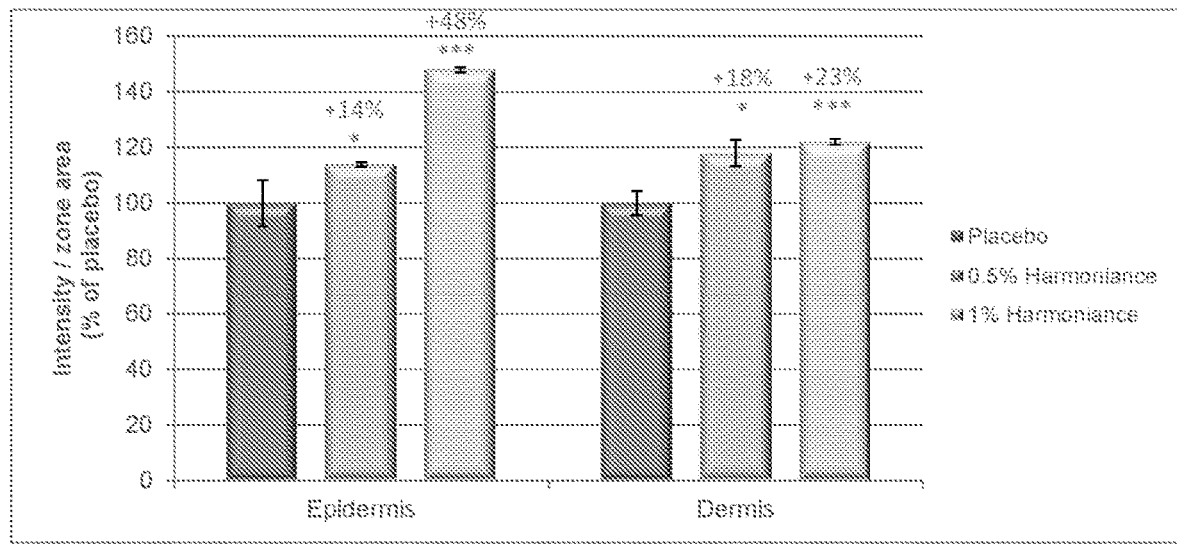
FIG. 4 is a graph of the results from quantification of hyaluronic acid fluorescent staining with respect to one embodiment of a *Nelumbo nucifera* (Sacred Lotus) serum fraction of the present invention.

Results:

Quantification of hyaluronic acid fluorescent staining is shown in FIG. 4. With Volocity* image analysis software. Statistical analyses were expressed versus placebo. (Mean±sem; n=3; *: significant; : very significant; *: highly significant with Student's t-test). This experiment was confirmed on two others donors.

Conclusion:

Ex vivo result suggested an increased hyaluronic acid fluorescent staining when skin biopsies were treated with Harmoniance at 1% for 48 hours.

B. Filaggrin Immunofluorescent Staining in Skin Biopsies

Skin Biopsies:

Normal human skin came from a plastic surgery intervention on the breast of a 53-year-old female. Skin biopsies were obtained with a 6 mm diameter punch (pfm medical). They were cultivated on culture medium containing 50% of DMEM 1 g/L glucose (Lonza) and 50% of Ham's-F12 (Lonza) supplemented with 10% of FBS (Lonza), 2 mM of L-glutamine (Lonza) and 100 µg/mL of Primocin* (InvivoGen). Skin biopsies were maintained at 37° C. in a humidified atmosphere containing 5% of $CO_2$.

Additional experiment was performed on the arm skin of a 64-year-old female donor.

Antibodies:

The primary antibody applied for this study was: Anti-filaggrin (Santacruz) mouse monoclonal, diluted at 1/100, for an hour and a half. The secondary antibody used was: Alexa Fluor* 488 donkey anti-mouse (Invitrogen), diluted at 1/1000, for one hour.

Principle:

Immunofluorescence is a technique allowing the visualization of a specific protein in tissue sections by binding a specific primary antibody. A secondary antibody labeled with fluorochrome is used to recognize the primary antibody. Immunofluorescence stained samples are then examined under a fluorescence microscope. A counterstain with DAPI allows to visualize cell nuclei and localize the epidermis.

Treatments:

Skin biopsies were treated, in duplicate, with PBS (Lonza) in placebo condition or with Harmoniance at 1%, twice a day, for 48 hours. 20 µL of solutions were applied on the top of the biopsies.

Biopsy Preparation:

To allow preservation and section of skin, tissues were fixed for 4 hours in buffered 10% formalin. Samples were transferred to baths with ethanol progressively concentrated to remove water, then followed by two baths of xylene to remove the alcohol, and finally embedded in molten paraffin wax. Embedded skin biopsies were then cut with a microtome (Shandon) into 4 µm thick sections and placed on Polysine* slides (Thermo Scientific).

Protocol:

Sections were deparaffinized and rehydrated with several successive xylene, alcohol and water baths. Then, an unmasking protocol was performed including 0.25% pepsin (Zymed, Invitrogen)/digestion for 15 minutes at 37° C. After a PBS wash and saturation of unspecific sites with a solution of 5% BSA (Sigma) during 30 minutes, the primary antibody was applied and the slides were incubated under agitation, at room temperature, in a damp room. After having rinsed the slides with PBS, the secondary antibody was applied, in the dark, under agitation, at room temperature, in a damp room. Finally, the cell nuclei were stained with 4',6'-diamidino-2-phenylindole (DAPI, Molecular Probes*) at 0.3 µM for 5 minutes and the sections mounted in Fluoromount-G* (Electron Microscopy Sciences). Detection was managed and examined using a Zeiss Axiovert 200M microscope with a 20× objective. Photos were taken with a Qimaging* EXI blue camera coupled to Volocity* acquisition software (Improvision).

Image Quantification:

Three photos per condition were analyzed with Volocity* image analysis software (Improvision), which allows to select the interesting zone thanks to the fluorescence intensity. The results obtained were the sum of green pixel intensities in the selected zone. Finally, for each photo, the sum obtained was adjusted by considering the length of the examined epidermis zone.

Statistical Analyses:

Statistical analyses were performed using JMP* 11 software (SAS) and Student's t test for independent samples with one-tailed direction of rejection. $p \leq 0.05$ were considered as significant, $p \leq 0.01$ as very significant and $p \leq 0.005$ as highly significant.

Figure 5:
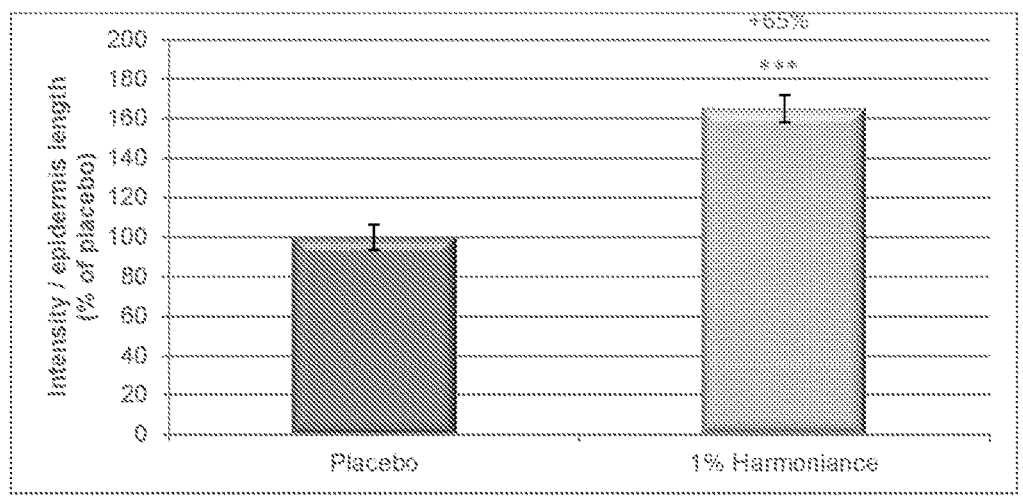
FIG. 5 is a graph of the results from quantification of filaggrin fluorescent staining with respect to one embodiment of a *Nelumbo nucifera* (Sacred Lotus) serum fraction of the present invention.

Results:

Quantification of filaggrin fluorescent staining is shown in FIG. 5. With Volocity* image analysis software. Statistical analyses were expressed versus placebo. (Mean±sem; n=3; ***: highly significant with Student's t-test). This experiment was confirmed on another donor.

Conclusion:

We observed an enhancement of filaggrin fluorescent intensity in skin biopsies treated with 1% Harmoniance for 48 hours compared to placebo-treated ones.

C. AQP3 Imunofluorescent Staining in Skin Biopsies

Skin Biopsies:

Normal human skin came from a plastic surgery intervention on the breast of a 53-year-old female. Skin biopsies were obtained with a 6 mm diameter punch (pfm medical). They were cultivated on culture medium containing 50% of DMEM 1 g/L glucose (Lonza) and 50% of Ham's-F12 (Lonza) supplemented with 10% of FBS (Lonza), 2 mM of L-glutamine (Lonza) and 100 µg/mL of Primocin* (InvivoGen). Skin biopsies were maintained at 37° C. in a humidified atmosphere containing 5% of $CO_2$.

Additional experiment was performed on the arm skin of a 64-year-old female donor.

Antibodies:

The primary antibody applied for this study was: Anti-AQP3 (Santacruz) goat polyclonal, diluted at 1/100, for an hour and a half. The secondary antibody used was: Alexa Fluor* 488 donkey anti-goat (Invitrogen), diluted at 1/1000, for one hour.

Principle:

Immunofluorescence is a technique allowing the visualization of a specific protein in tissue sections by binding a specific primary antibody. A secondary antibody labeled with fluorochrome is used to recognize the primary antibody. Immunofluorescence stained samples are then examined under a fluorescence microscope.

Treatments:

Skin biopsies were treated, in duplicate, with PBS (Lonza) in placebo condition or with Harmoniance at 1%, twice a day, for 48 hours. 20 µL of solutions were applied on the top of the biopsies.

Biopsy Preparation:

To allow preservation and section of skin, tissues were fixed for 4 hours in buffered 10% formalin. Samples were transferred to baths with ethanol progressively concentrated to remove water, then followed by two baths of xylene to remove the alcohol, and finally embedded in molten paraffin wax. Embedded skin biopsies were then cut with a microtome (Shandon) into 4 µm thick sections and placed on Polysine* slides (Thermo Scientific).

Protocol:

Sections were deparaffinized and rehydrated with several successive xylene, alcohol and water baths. Then, an unmasking protocol was performed including microwave exposure at 600 W in citrate buffer 0.01 M pH 6 (Sigma) until boiling. After a PBS wash and saturation of unspecific sites with a solution of 5% BSA (Sigma) during 30 minutes, the primary antibody was applied and the slides were incubated under agitation, at room temperature, in a damp room. After having rinsed the slides with PBS, the secondary antibody was applied, in the dark, under agitation, at room temperature, in a damp room. Finally, the sections were mounted in Fluoromount-G* (Electron Microscopy Sciences). Detection was managed and examined using a Zeiss Axiovert 200M microscope with a 20× objective. Photos were taken with a Qimaging* EXI blue camera coupled to Volocity* acquisition software (Improvision).

Image Quantification:

Eight photos per condition were analyzed with Volocity* image analysis software (Improvision), which allows to select the interesting zone thanks to the fluorescence intensity. The results obtained were the sum of green pixel intensities in the selected zone. Finally, for each photo, the sum obtained was adjusted by considering the area of the examined epidermis zone.

Statistical Analyses:

Statistical analyses were performed using JMP* 11 software (SAS) and Student's t test for independent samples with one-tailed direction of rejection. p≤0.05 were considered as significant, p≤0.01 as very significant and p≤0.005 as highly significant.

Figure 6:
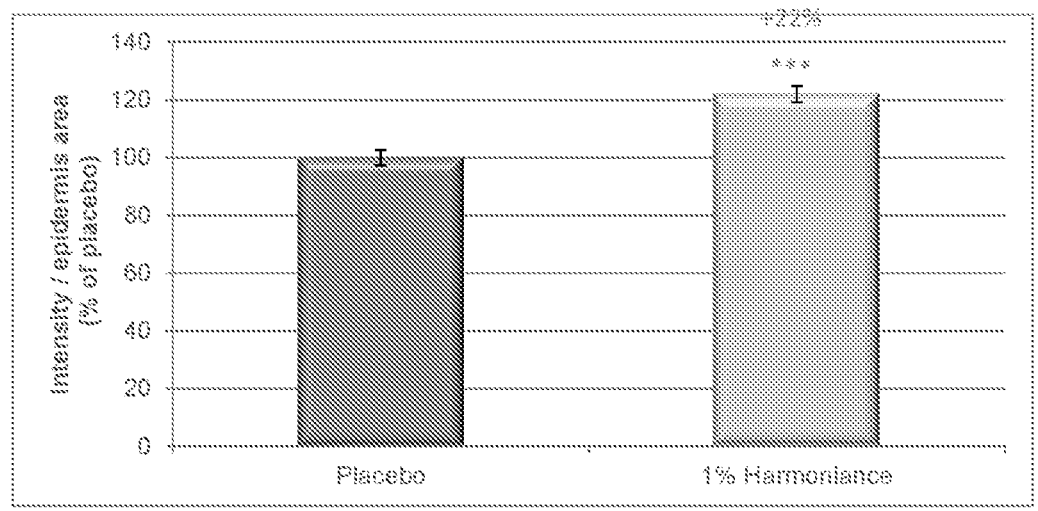
FIG. 6 is a graph of the results from quantification of AQP3 fluorescent staining with respect to one embodiment of a *Nelumbo nucifera* (Sacred Lotus) serum fraction of the present invention.

Results:

Quantification of AQP3 fluorescent staining is shown in FIG. 6. With Volocity* image analysis software. Statistical analyses were expressed versus placebo. (Mean±sem; n=8; ***: highly significant with Student's t-test). This experiment was confirmed on another donor.

Conclusion:

We observed an enhancement of AQP3 fluorescent intensity in skin biopsies treated with 1% Harmoniance for 48 hours compared to placebo-treated ones.

D. Evaluation of Skin Barrier Function in Reconstructed Epidermis

Reconstructed Human Epidermis (RHE):

The keratinocytes used for this study were serum fractioned from the foreskin of a 3-year-old donor. They were grown in Serum Free Medium and 100 µg/ml of Primocin* (InvivoGen). Cells were maintained at 37° C. in a humidified atmosphere containing 5% of $CO_2$. Then, cells were seeded on inert polycarbonate membrane (0.5 cm² insert, Nunc) and were air-lifted during 12 days on a chemically defined medium (Rosdy M. and Clauss L. C., 1990; Rosdy M. et al., 1993) at 37° C. in a humidified atmosphere containing 5% of $CO_2$.

Additional data were obtained with keratinocytes serum fractioned from the foreskin of a 3-year-old donor and from the abdominal skin of a 24-year-old donor.

Reagent:

The fluorescent dye used for this study is lucifer yellow (Santacruz).

Principle:

The lucifer yellow dye allows to evaluate the skin barrier integrity, the penetration of the dye in the epidermal layers is correlated with the permeability of the skin barrier.

Treatments:

After 17 days of post-reconstruction, RHEs were topically stressed, or not, 3 hours with 0.15% SDS (Sigma) then treated with PBS (Lonza) in placebo condition or with Harmoniance at 0.5% or 1%, twice a day, for 48 hours. After PBS-rinse, 1 mM of lucifer yellow fluorescent dye was added and incubated for 1 hour. RHEs were washed again with PBS and removed from their insert.

RHE Preparation:

To allow preservation of RHEs, they were fixed for 4 hours in buffered 10% formalin. Samples were transferred to baths with ethanol progressively concentrated to remove water, then followed by two baths of xylene to remove the alcohol, and finally embedded in molten paraffin wax. Embedded RHE were then cut with a microtome (Shandon) into 4 µm thick sections and placed on slides (Thermo Scientific).

Protocol:

Sections were deparaffinized and rehydrated with several successive xylene, alcohol and water baths. Finally, the cell nuclei were stained with 4',6'-diamidino-2-phenylindole (DAPI, Molecular Probes*) at 0.3 µM for 5 minutes and slides were mounted in Fluoromount-G* (Electron Microscopy Sciences) for imaging. Detection was managed and examined using a Zeiss Axiovert 200M microscope with a 20× objective. Photos were taken with a Qimaging* EXI blue camera coupled to Volocity* acquisition software (Improvision).

Image Quantification:

Three photos per condition were analyzed with Volocity* image analysis software (Improvision), which allows to select the interesting zone thanks to the fluorescence intensity. The results obtained were the area of fluorescence. Finally, for each photo, the result obtained was adjusted by considering the area of the global epidermis zone.

Statistical Analyses:

Statistical analyses were performed using JMP* 11 software (SAS) and Student's t test for independent samples with one-tailed direction of rejection. p≤0.05 were considered as significant, p≤0.01 as very significant and p≤0.005 as highly significant.

Figure 7:
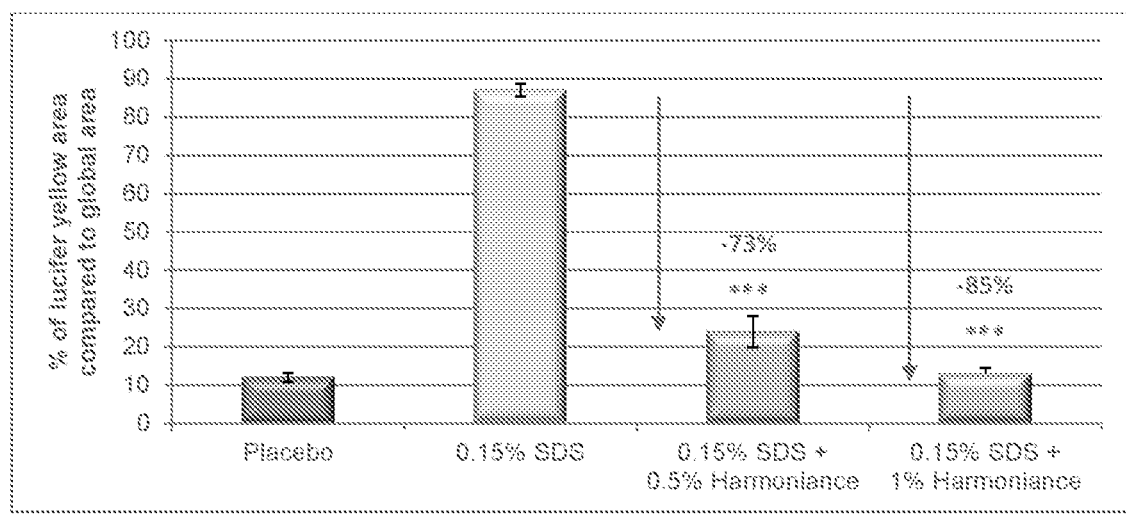
FIG. 7 is a graph of the results from quantification of fluorescent dye penetration with respect to one embodiment of a *Nelumbo nucifera* (Sacred Lotus) serum fraction of the present invention.

Results:

Quantification of fluorescent dye penetration is shown in FIG. 7. With Volocity* image analysis software. Statistical analyses were expressed versus 0.15% SDS. (Mean±sem; n=3; ***: highly significant with Student's t-test). This experiment was confirmed on two other donors.

Conclusion:

We observed an improvement of skin barrier recovery with 1% Harmoniance treatment, after SDS stress on reconstructed epidermis.

F. Collagen I Immunofluorescent Staining on Fibroblasts

Fibroblasts:

The fibroblasts used for this study were extracted from normal human skin of a 53-year-old female donor. They were grown in DMEM 1 g/L glucose (Lonza) supplemented with 10% of FBS (Lonza), 2 mM of L-Glutamine (Lonza) and 100 µg/mL of Primocin* (InvivoGen). Cells were maintained at 37° C. in a humidified atmosphere containing 5% of $CO_2$.

Antibodies:

The primary antibody applied for this study was: Anti-Collagen I (Rockland) rabbit polyclonal, diluted at 1/100, for an hour and a half. The secondary antibody used was: Alexa Fluor* 488 donkey anti-rabbit (Invitrogen), diluted at 1/1000, for one hour.

Principle:

Immunofluorescence is a technique allowing the visualization of a specific protein in cells by binding a specific primary antibody. A secondary antibody labeled with fluorochrome is used to recognize the primary antibody Immunofluorescence stained samples are then examined under a fluorescence microscope. A counterstain with DAPI allows to visualize cell nuclei.

Cell Preparation:

Cells were seeded in 8 well glass chamber slide (Falcon). Two wells were analyzed per condition.

Treatments:

Cells were treated, or not, in duplicate, with Harmoniance at 0.01% directly diluted in the culture medium, twice a day, for 48 hours.

Protocol:

After treatments, cells were rinsed with PBS and fixed with cold methanol for 4 minutes at 4° C. Cells were then incubated with the primary antibody, under agitation, at room temperature. After three PBS-washes, the fluorescent secondary antibody was applied, in the dark, under agitation, at room temperature. After three other washes with PBS, the cell nuclei were stained with 4',6'-diamidino-2-phenylindole (DAPI, Molecular Probes*) at 0.3 µM for 5 minutes and slides were mounted in Fluoromount-G* (Electron Microscopy Sciences). Detection was managed and examined using a Zeiss Axiovert 200M microscope with a 20× objective. Photos were taken with a Qimaging* EXI blue camera coupled to Volocity* acquisition software (Improvision).

Image Quantification:

Three photos per condition were analyzed with Volocity* image analysis software (Improvision), which allows to select the cells thanks to the collagen I fluorescence intensity. The results obtained were the sum of green pixel intensities in the selected zone. Finally, for each photo, the sum obtained was adjusted by considering the area of the cells.

Statistical Analyses:

Statistical analyses were performed using JMP* 11 software (SAS) and Student's t test for independent samples with one-tailed direction of rejection. $p \leq 0.05$ were considered as significant, $p \leq 0.01$ as very significant and $p \leq 0.005$ as highly significant.

Figure 8:
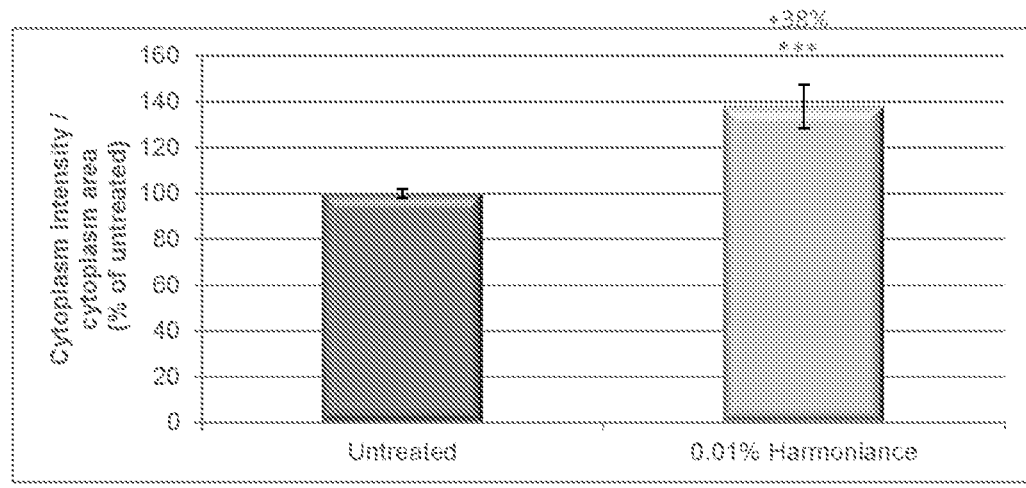
FIG. 8 is a graph of the results from quantification of collagen I fluorescent staining with respect to one embodiment of a *Nelumbo nucifera* (Sacred Lotus) serum fraction of the present invention.

Results:

Quantification of collagen I fluorescent staining is shown in FIG. 8. With Volocity* image analysis software. Statistical analyses were expressed versus untreated. (Mean±sem; n=3; ***: highly significant with Student's t-test).

Conclusion:

We observed a statistically significant in vitro enhancement in collagen I fluorescent intensity on fibroblasts treated with 0.01% Harmoniance for 48 hours.

G. Elastic Fibers after UV Stress in Skin Biopsies

Skin Biopsies:

Normal human skin came from a plastic surgery intervention on the breast of a 30-year-old female. Skin biopsies were obtained with a 6 mm diameter punch (pfm medical). They were cultivated on culture medium containing 50% of DMEM 1 g/L glucose (Lonza) and 50% of Ham's-F12 (Lonza) supplemented with 10% of FBS (Lonza), 2 mM of L-glutamine (Lonza) and 100 µg/mL of Primocin* (InvivoGen). Skin biopsies were maintained at 37° C. in a humidified atmosphere containing 5% of $CO_2$.

Reagents:

Elastica Van Gieson staining kit (Merck) was used to stain the elastic fibers.

Principle:

The resorcinol-fuchsin solution, according to Weigert, in combination with a van Gieson's picrofuchsin solution allows the visualization of elastic fibers (in black-purple) and collagen (in red-pink).

Treatments:

Skin biopsies were treated, or not, in duplicate, with Harmoniance at 1%, twice a day, for 48 hours. 20 µl of solutions were applied on the top of the biopsies. Then skin biopsies were stressed with a single dose of 5 $J/cm^2$ UVA and 200 $mJ/cm^2$ UVB and re-incubated for 10 hours before staining. A UVA oven type BLX-E365 and a UVB oven type BLX-E312 (Fisher Bioblock Scientific) were used.

Biopsy Preparation:

To allow preservation and section of skin, tissues were fixed for 4 hours in buffered 10% formalin. Samples were transferred to baths with ethanol progressively concentrated to remove water, then followed by two baths of xylene to remove the alcohol, and finally embedded in molten paraffin wax. Embedded skin biopsies were then cut with a microtome (Shandon) into 4 µm thick sections and placed on Polysine* slides (Thermo Scientific).

Protocol:

Sections were deparaffinized and rehydrated with several successive xylene, alcohol and water baths. After a PBS wash, the sections were incubated in resorcinol-fuchsin solution according to Weigert for 15 minutes. The sections were washed in water for 5 minutes. A picrofuchsin solution according to Van Gieson was applied on sections for 2 minutes. After several successive water, alcohol and xylene baths, slides were mounted in Eukitt* (O. Kindler) and examined using an Eclipse E600 microscope (Nikon) with a 40× objective. Photos were taken with a QImaging* EXI blue camera and processed by using the Q-Capture Pro 7 software (QImaging*).

Conclusion:

A better organization of elastic fibers was observed when the skin was pretreated with Harmoniance at 1%.

H. Glycerol Release Assay in 3T3-L1 Adipocytes

3T3-L1 Adipocytes:

3T3-L1 pre-adipocytes (ATCC) (PX+8) were cultured in DMEM 4.5 g/L glucose (Lonza) supplemented with 10% of FBS (Lonza), 2 mM of L-Glutamine (Lonza) and 100 µg/mL of Primocin* (InvivoGen).

2 days after the cells' confluence, differentiation into adipocytes was induced by adding 0.5 mM IBMX, 1 µM dexamethasone and 10 µg/ml insulin (Sigma) in the culture medium for 3 days. Afterwards, IBMX and dexamethasone were removed and only the insulin was maintained for 3 to 4 days; then, the insulin was also removed, and the cells were maintained in culture medium for another 3 days.

Reagents:

Glycerol release was measured using Adipolysis Assay Kit (Cayman Chemical).

Principle:

Lipolysis is the hydrolysis of triglycerides into glycerol and fatty acids. The amount of glycerol release will be proportional to both the amount of stored triglyceride and the degree of lipolysis.

Cell Preparation:

Cells were seeded in 24 well plate (Thermo Fisher Scientific).

Treatments:

Differentiated cells were treated, or not, in duplicate, with Harmoniance at 0.01% directly diluted in the culture medium or with caffeine at 2 mM, once a day, for 48 hours.

Protocol:

Assay was performed using supplier recommendations.

Statistical Analyses:

Statistical analyses were performed using JMP* 11 software (SAS) and Student's t test for independent samples with one-tailed direction of rejection. $p \leq 0.05$ were considered as significant, $p \leq 0.01$ as very significant and $p \leq 0.005$ as highly significant.

Figure 9:
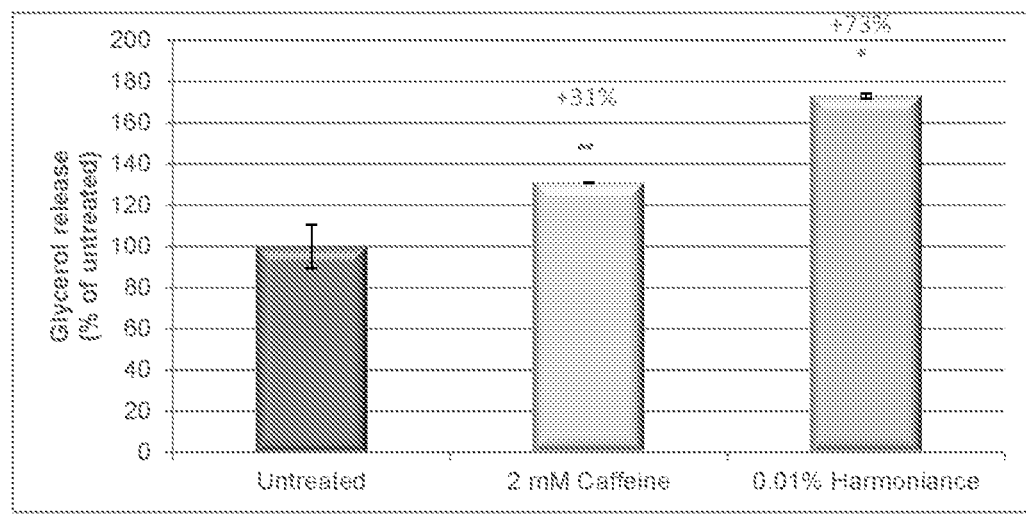
FIG. 9 is a graph of the results from quantification of glycerol release in differentiated 3T3-L1 with respect to one embodiment of a *Nelumbo nucifera* (Sacred Lotus) serum fraction of the present invention.

Results:

Quantification of glycerol release in differentiated 3T3-L1 is shown in FIG. 9. Statistical analyses were expressed versus untreated. (Mean±sem; n=2; ~: nearly significant; *: significant with Student's t-test). This experiment was confirmed on two others donors.

Conclusion:

We observed a statistically significant in vitro enhancement in glycerol release of 3T3-L1 treated with 0.01% Harmoniance for 48 hours.

I. Melanin Staining in Skin Biopsies

Skin Biopsies:

Normal human skin came from a plastic surgery intervention on the breast of a 52-year-old female. Skin biopsies were obtained with a 6 mm diameter punch (pfm medical). They were cultivated on culture medium containing 50% of DMEM 1 g/L glucose (Lonza) and 50% of Ham's-F12 (Lonza) supplemented with 10% of FBS (Lonza), 2 mM of L-glutamine (Lonza) and 100 μg/mL of Primocin* (InvivoGen). Skin biopsies were maintained at 37° C. in a humidified atmosphere containing 5% of $CO_2$.

Additional experiment was performed on the abdominal skin of a 60-year-old female donor.

Reagents:

The Fontana-Masson staining requires stock solution preparation which is formed by adding ammonium hydroxide (Acros Organics) to a solution of silver nitrate (Sigma). This solution was left to settle for 24 hours before use.

Principle:

The melanins are a group of brown-black pigments which are bound to proteins. Melanins are synthetized by melanocytes in melanosomes, and are then transmitted to keratinocytes of the basal epidermis where they form caps above the nuclei.

The Fontana-Masson staining is based on the melanin ability to reduce solutions of ammoniacal silver nitrate to metallic silver (brown) without the use of an external reducing agent.

Treatments:

Skin biopsies were treated, or not, in duplicate, with Harmoniance at 0.5%-1%-3% or with 20 mM kojic acid, twice a day, for 48 hours. 20 μl of solutions were applied on the top of the biopsies.

Biopsy Preparation:

To allow preservation and section of skin, tissues were fixed for 4 hours in buffered 10% formalin. Samples were transferred to baths with ethanol progressively concentrated to remove water, then followed by two baths of xylene to remove the alcohol, and finally embedded in molten paraffin wax. Embedded skin biopsies were then cut with a microtome (Shandon) into 4 μm thick sections and placed on Polysine* slides (Thermo Scientific).

Protocol:

Sections were deparaffinized and rehydrated with several successive xylene, alcohol and water baths. Then, 100 μl of stock solution were added on each section and slides were incubated 10 minutes at 60° C. After distilled water wash during 3 minutes, biopsies were incubated with 100 μl of 5% sodium thiosulfate (Sigma) during 2 minutes. Slides were washed during 3 minutes in a distilled water bath and finally dehydrated in several alcohol and xylene baths. They were mounted in Eukitt* (O. Kindler) and examined using an Eclipse E600 microscope (Nikon) with a 20× objective. Photos were taken with a QImaging* EXI blue camera and processed by using the Q-Capture Pro 7 software (QImaging*).

Image Quantification:

Three images per condition were analyzed. ImageJ software allows to select the interesting zone and generates a histogram representing the pixel number per intensity in this zone. Thus, the sum of all dark pixels (having intensity between 0 and 175) was calculated and the sum obtained was adjusted to the length of the examined epidermis zone. (McMullen R. L. et al., 2010)

Statistical Analyses:

Statistical analyses were performed using JMP* 11 software (SAS) and Student's t test for independent samples with one-tailed direction of rejection. $p \leq 0.05$ were considered as significant, $p \leq 0.01$ as very significant and $p \leq 0.005$ as highly significant.

Figure 10:
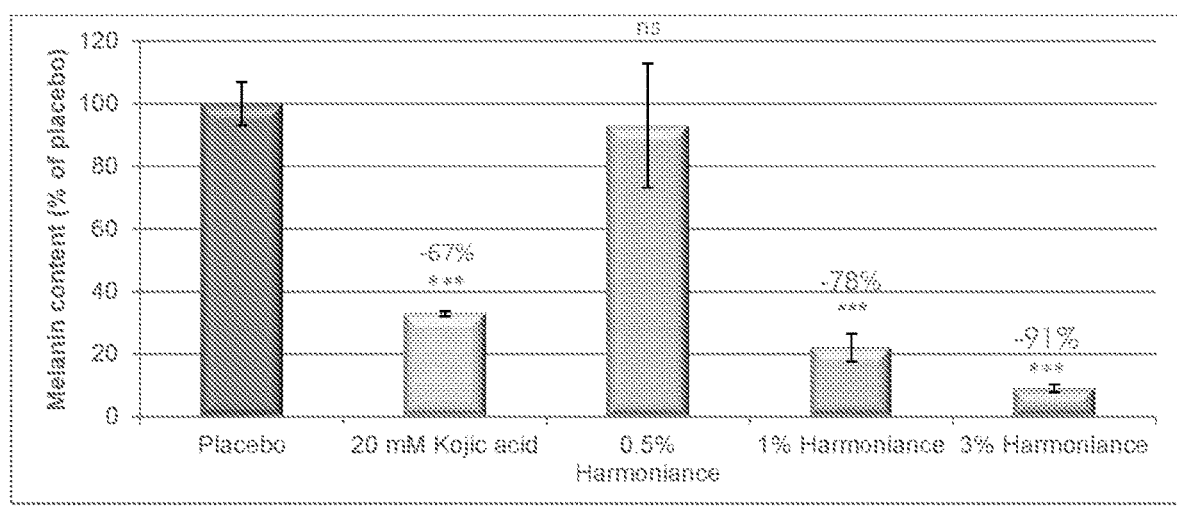
FIG. 10 is a graph of the results from quantification of Fontana Masson staining with respect to one embodiment of a *Nelumbo nucifera* (Sacred Lotus) serum fraction of the present invention.

Results:

Quantification of Fontana Masson staining is shown in FIG. 10. With ImageJ analysis software. Statistical analyses were expressed versus placebo. (Mean±sem; n=3; ns: non significant; ***: highly significant with Student's t-test). This experiment was confirmed on another donor.

Conclusion:

Harmoniance at 1% and 3% significantly helps decrease melanin content.

J. General Conclusion

This example summarizes the efficacy tests of Harmoniance in vitro (on cultured fibroblasts and 3T3-L1 adipocytes), on reconstructed human epidermis and ex vivo (on normal human skin). Markers of hydration and barrier function, skin laxity, drainage and pigmentation were investigated.

In the first part, the effect of Harmoniance at 1% was observed on the expression of hyaluronic acid, filaggrin and AQP3 proteins in ex vivo skin. After 48 hours of Harmoniance application, the expression of these skin hydration markers was increased.

Then, the skin barrier function was evaluated on reconstructed epidermis treated with 1% Harmoniance after a SDS stress. A 48-hour treatment with Harmoniance allows to counteract the SDS stress effect.

Next, the effect of Harmoniance was studied on collagen and elastin, markers of skin laxity. We observed an increase in collagen I expression in fibroblasts after 48-hour treatment with 0.01% Harmoniance. Moreover, after a combined UVA and UVB stress on ex vivo skin, a better organization of elastic fibers was shown when the skin was pre-treated with Harmoniance at 1% for 48 hours.

In the third part, Harmoniance effect was investigated on glycerol release, indicator of drainage capacity. To do so, glycerol release was examined on 3T3-L1 pre-adipocytes. After 0.01% Harmoniance treatment for 48 hours on differentiated cells, an enhancement of glycerol release was detected.

In the last part, skin pigmentation was evaluated after Harmoniance treatment for 48 hours. A decrease in melanin content was observed in a dose-dependent manner.

Harmoniance targets the most important attributes of skin appearance associated with skin aging, including hydration and barrier function, skin laxity and appearance of wrinkles, drainage and body contouring, skin pigmentation and tone.

The examples above are non-limiting examples of certain embodiments of bioactive formulations of the present invention. The examples are given solely for the purpose of illustration and are not to be construed as limitations of the present invention, as many variations thereof are possible without departing from the spirit and scope of the invention, which would be recognized by one of ordinary skill in the art. In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minor materials will vary depending on the physical and chemical characteristics of the particular ingredients selected to make the present invention as described herein.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

Citation of a reference herein shall not be construed as an admission that such reference is prior art to the present invention. All references cited herein are hereby incorporated by reference in their entirety.

What is claimed is:

1. A method of improving skin appearance associated with skin aging by mitigating the adverse effects of full spectrum sunlight exposure on skin cells, said method comprising the step of topically applying an anti-aging bioactive composition to a skin surface wherein said bioactive composition consists of i) a dermatologically acceptable carrier and ii) an effective amount of *Nelumbo nucifera* (Sacred Lotus) stabilized serum fraction, wherein said *Nelumbo nucifera* serum fraction is isolated using a fractionation process comprising subjecting plant cell juice derived from fresh plant biomass of the fresh (living) whole plants of *Nelumbo nucifera* to an electromagnetic field at a frequency of greater than 2.45 GHz for a time effective to destabilize the plant cell juice yielding a coagulated cell juice mixture comprising a coagulated membrane fraction, and separating said coagulated membrane fraction from said coagulated cell juice mixture in order to yield a bioactive fraction comprising a cytoplasm/cytosole fraction that is substantially-free from said membrane fraction, followed by additional treatments enabling to separate cytoplasm fraction from cytosole fraction, and mixing the cytosole fraction with stabilizing agents to yield a *Nelumbo nucifera* stabilized serum fraction, wherein said *Nelumbo nucifera* stabilized serum fraction has a dry matter ranging from between 6.59-6.78% w/w, a total soluble sugars ranging from between 2.29-2.54% w/w and a total phenolic compound ranging from 1.33-1.58% w/w; and wherein said bioactive composition has properties on the skin selected from the group consisting of: increasing the expression of hyaluronic acid, filaggrin and AQP3 proteins, improving hydration, improving skin recovery after SDS stress, increasing the expression of collagen I, increasing the expression of filaggrin, improving organization of elastin fibers and decreasing melanin content, wherein the said bioactive composition has a synergistic combination of properties selected from the group consisting of the following: (i) beneficial spectral absorbance characteristics in UVA-UVB area; (ii) high UVA:UVB absorbance ratios in conjunction with broad UVA and UVB spectral absorption photostability demonstrated after full spectrum simulated sun exposures; (iii) increased attenuation in UVA1 area and simultaneous increase in UVA/UVB ratio as radiation dose is increased; (iv) potent biological activities (properties) demonstrated in in vitro cell culture based ELISA (Enzyme-Linked ImmunoSorbent Assays) which measure the amount of cytokines (IL-6), chemokines (IL-8) and prostaglandins ($PGE_2$) in response to full spectrum simulated sun exposure and relevant enzymatic models which measure the inhibition of elastase and MMP3 (Matrix Metalloproteinase-3) (v) maintenance of more than 95% of initial (pre-irradiation) DPPH (2,2-Diphenyl-1-Picrylhydrazyl) quenching capacities after 4 MED exposure delivered by full spectrum simulated sunlight; (vi) multifunctional activities that work together to mitigate various adverse effects of full spectrum sunlight exposure on skin cells.

2. The method of claim 1, wherein the bioactive composition comprises, by weight of the total composition, from 0.001% to 99% of said *Nelumbo nucifera* (Sacred Lotus) serum fraction.

3. The method of claim 1, wherein the said bioactive composition has multifunctional activities that work synergistically to mitigate adverse effects of full spectrum sunlight exposure on skin cells.

4. The method of claim 1, wherein the skin surface is selected from the group consisting of a body skin surface and a facial skin surface.

* * * * *